(12) United States Patent
Chiang et al.

(10) Patent No.: US 7,132,572 B2
(45) Date of Patent: Nov. 7, 2006

(54) FULLERENE COMPOUNDS

(75) Inventors: Long Y. Chiang, 3 Tuttle Dr., Acton, MA (US) 01720; Loon-Seng Tan, Centerville, OH (US)

(73) Assignee: Long Y. Chiang, Acton, MA (US)

( * ) Notice: Subject to any disclaimer, the term of this patent is extended or adjusted under 35 U.S.C. 154(b) by 113 days.

(21) Appl. No.: 10/620,839

(22) Filed: Jul. 16, 2003

(65) Prior Publication Data

US 2005/0191229 A1    Sep. 1, 2005

Related U.S. Application Data

(60) Provisional application No. 60/396,782, filed on Jul. 17, 2002.

(51) Int. Cl.
*C07C 211/61* (2006.01)
(52) U.S. Cl. .................. 564/427; 977/734
(58) Field of Classification Search ............. 564/427; 977/734
See application file for complete search history.

(56) References Cited

U.S. PATENT DOCUMENTS

| 5,378,519 A | * | 1/1995 | Kikuchi et al. ............. 428/690 |
| 6,020,523 A | | 2/2000 | Chiang ..................... 562/493 |

OTHER PUBLICATIONS

Long Y. Chang, et al. "Synthesis of $C_{60}$diphenylaminofluorene dyad with large 2PA cross-sections sand efficient intramolecular two-photon energy transfer" Jul. 24, 2002 Published on web as an Advance Article.

* cited by examiner

*Primary Examiner*—Kamal A. Saeed
*Assistant Examiner*—Joseph R. Kosack

(57) ABSTRACT

The invention relates to fullerene compounds of the following formula:

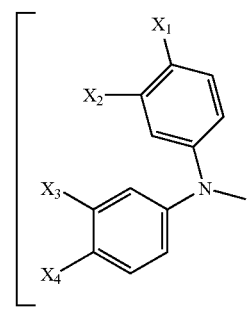

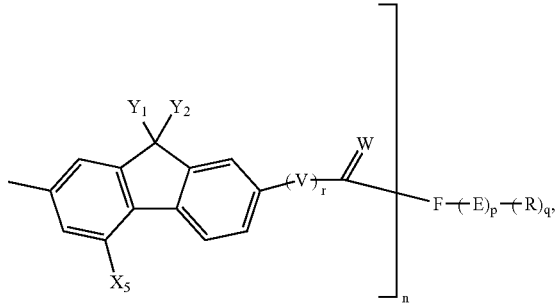

in which $X_1$, $X_2$, $X_3$, $X_4$, $X_5$, $Y_1$, $Y_2$, V, W, F, E, R, r, n, p, and q are defined as in the specification. Also disclosed are pharmaceutical compositions containing one of the compounds described above.

17 Claims, No Drawings

FULLERENE COMPOUNDS

CROSS REFERENCE TO RELATED APPLICATIONS

This application claims the benefit of U.S. Provisional Application No. 60/396,782, filed Jul. 17, 2002. The contents of this applications is hereby incorporated herein by reference in its entirety.

BACKGROUND OF THE INVENTION

Free radicals have been shown to inhibit tumor growth by causing oxidative damage to lipids, proteins, and nucleic acids of the tumor cells. In clinical practice, a photosensitizer is first delivered to a tumor site and then activated by irradiation to generate free radicals, thus inhibiting tumor growth. Fullerenes are conjugated olefins of a closed cage structure. When photo-excited, they are capable of transforming molecular oxygen into singlet oxygen and then the related free radicals, such as superoxide free radicals, i.e., $O_2^-$. Thus, fullerenes may be used to treat tumors.

SUMMARY OF THE INVENTION

The present invention relates to fullerene compounds of formula (I):

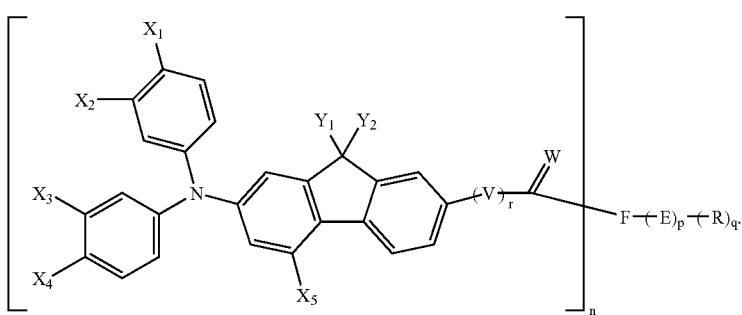

(I)

Referring to formula (I), F is a fullerene core; E is $Y_1,Y_2$-amino, $Y_2$-amino, $(Y_1,Y_2$-alkyl)-amino, $Y_1,Y_2$-ethylenediamino, (dihydroxymethyl)alkylamino, $(X_1,X_3$-aryl)amino, $X_1,X_3$-aryloxy, $Y_2$-alkoxy, $Y_1,Y_2$-alkoxy, $(Y_1,Y_2$-amino)alkoxy, $(Y_1,Y_2,Y_3$-aryl)oxy, (dihydroxyalkyl)-aryloxy, $(Y_1,Y_2,Y_3$-alkyl)amino, $(Y_1,Y_2, Y_3$-aryl)amino, dihydroxyalkylamino, $Y_1,Y_2,Y_3$-alkoxy, (trihydroxyalkyl)alkoxy, (trihydroxyalkyl)alkylamino, (dicarboxyalkyl)amino, $Y_2$-thio, $(Y_1,Y_2,Y_3$-alkyl)thio, $(X_1,X_3$-aryl)thio, $(Y_1,Y_2$-alkyl)thio, (dihydroxyalkyl)thio, $Y_1,Y_2$-dioxoalkyl, tri-$(Y_1,Y_2,Y_3$-methylaminocarboxyethyl)methylamino, ((glycosidyl)oxoheteroaryl)amino, ((glycosidyl)oxoaryl)amino, $(X_1,X_2,X_3$-heteroaryl)amino, $(X_1$-diarylketone)amino, $(T,X_1$-oxoaryl)amino, $(T,X_1$-dioxoaryl)amino, $(Y_1$-alkyl, $Y_2$-alkyldioxoheteroaryl)amino, $(Y_1$-alkyl,$Y_2$-alkyldioxoaryl)amino, $(di(Y_1,Y_2$-methyl)dioxoheteroaryl)amino, $(di(Y_1,Y_2$-methyl)dioxoaryl)amino, ((glycosidyl)heteroaryl)amino, ((glycosidyl)aryl)amino, ((carboxylacetylalkyl)oxo-heteroaryl)amino, ((carboxylacetylalkyl)oxoaryl)amino, ((isopropylaminohydroxy-alkoxy)aryl)amino, $(X_1,X_2,X_3$-alkylaryl)amino, $(X_1,X_2,X_3$-heteroaryl)oxy, (isopropylaminohydroxyalkyl)aryloxy, $(X_1,X_2,X_3$-oxoheteroaryl)oxy, $(X_1,X_2,X_3$-oxoaryl)oxy, $(X_1,Y_1$-oxoheteroaryl)oxy, $(X_1$-diarylketone)oxy, $(T,X_1$-oxoaryl)oxy, $(X_1,X_2$-dioxoaryl)oxy, $(Y_1,Y_2$,di-aminodihydroxy)alkyl, $(X_1,X_2$-heteroaryl)thio, ((tricarboxylalkyl)ethylene-diamino)alkoxy, $(X_1,X_2$-oxoaryl)thio, $(X_1,X_2$-dioxoaryl)thio, (glycosidylheteroaryl)thio, (glycosidylaryl)thio, $Y_1$-alkyl(thiocarbonyl)thio, $Y_1,Y_2$, -alkyl(thiocarbonyl)thio, $Y_1,Y_2,Y_3$-alkyl(thiocarbonyl)thio, $(Y_1,Y_2$-aminothiocarbonyl)thio, (pyranosyl)thio, cysteinyl, tyrosinyl, (phenylalainyl)amino, (dicarboxyalkyl)thio, (aminoaryl)$_{1-100}$amino, (pyranosyl)$_{1-100}$amino, $(Y_1$-aminoaryl)$_{1-100}$amino, (amino(sulfoaryl))$_{T100}$amino, peptidyl, thymidinyl, uridinyl, guanosinyl, adenosinyl, cholesteryl, or biotinylalkoxy; in which T is halo; each of $X_1, X_2, X_3, X_4$, and $X_5$, independently (as part of E or as a substituent itself), is $-Y_2$, $-O-Y_2$, $-S-Y_2$, $-NH-Y_2$, $-CO-O-Y_2$, $-O-CO-Y_2$, $-CO-NH-Y_2$, $-CO-NY_1Y_2$, $-NH-CO-Y_2$, $-SO_2-Y_2$, $-SO_2-O-Y_2$, $-CHY_1Y_2$, or $-NY_1Y_2$; each of $Y_1, Y_2$, and $Y_3$, independently (as part of E or a substitutent itself) or taken together, is $-B-Z$ or $-Z$; in which each B, independently, is $-R^a-O-[Si(CH_3)_2-O-]_{1-100}$, $C_{1-2000}$ alkyl, $C_{6-40}$ aryl, $C_{7-2000}$ alkylaryl, $C_{7-2000}$ arylalkyl, $(C_{1-30}$ alkyl ether)$_{1-100}$, $(C_{6-40}$ aryl ether)$_{1-100}$, $(C_{7-2000}$ alkylaryl ether)$_{1-100}$, $(C_{7-2000}$ arylalkyl ether)$_{1-100}$, $(C_{1-30}$ alkyl thioether)$_{1-100}$, $(C_{6-40}$ aryl thioether)$_{1-100}$, $(C_{7-2000}$ alkylaryl thioether)$_{1-100}$, $(C_{7-2000}$ arylalkyl thioether)$_{1-100}$, $(C_{2-50}$ alkyl ester)$_{1-100}$, $(C_{7-2000}$ aryl ester)$_{1-100}$, $(C_{8-2000}$ alkylaryl ester)$_{1-100}$, $(C_{8-2000}$ arylalkyl ester)$_{1-100}$, $-R^a-CO-O-(C_{1-30}$ alkyl ether)$_{1-100}$, $-R^a-CO-O-(C_{6-40}$ aryl ether)$_{1-100}$, $-R^a-CO-O-(C_{7-2000}$ arylalkyl ether)$_{1-100}$, $-R^a-CO-O-(C_{7-2000}$ arylalkyl ether)$_{1-100}$, $(C_{4-50}$ alkyl urethane)$_{1-100}$, $(C_{14-60}$ aryl urethane)$_{1-100}$, $(C_{10-2000}$ alkylaryl urethane)$_{1-100}$, $(C_{10-2000}$ arylalkyl urethane)$_{1-100}$, $(C_{5-50}$ alkyl urea)$_{1-100}$, $(C_{14-60}$ aryl urea)$_{1-100}$, $(C_{10-2000}$ alkylaryl urea)$_{1-100}$, $(C_{10-2000}$ arylalkyl urea)$_{1-100}$, $(C_{2-50}$ alkyl amide)$_{1-100}$, $(C_{7-60}$ aryl amide)$_{1-100}$, $(C_{8-2000}$ alkylaryl amide)$_{1-100}$, $(C_{8-2000}$ arylalkyl amide)$_{1-100}$, $(C_{3-30}$ alkyl anhydride)$_{1-100}$, $(C_{8-50}$ aryl anhydride)$_{1-100}$, $(C_{9-2000}$ alkylaryl anhydride)$_{1-100}$, $(C_{9-2000}$ arylalkyl anhydride)$_{1-100}$, $(C_{2-30}$ alkyl carbonate)$_{1-100}$, $(C_{7-50}$ aryl carbonate)$_{1-100}$, $(C_{8-2000}$ alkylaryl carbonate)$_{1-100}$, $(C_{8-2000}$ arylalkyl carbonate)$_{1-100}$, $-R^a-O-CO-NH-(R^b$ or $Ar-R^b-Ar)-NH-CO-O-(C_{1-30}$ alkyl ether, $C_{6-40}$ aryl ether, $C_{7-2000}$ alkylaryl ether, or $C_{7-2000}$ arylalkyl ether)$_{1-100}$, —$R^a$—O—CO—NH—($R^b$ or Ar—$R^b$—Ar)—NH —CO—O—($C_{2-50}$ alkyl ester, $C_{7-60}$ aryl ester, $C_{8-2000}$ alkylaryl ester, or $C_{8-2000}$ arylalkyl ester)$_{1-100}$, —$R^a$—O—CO —NH—($R^b$ or Ar—$R^b$—Ar)—NH—CO—O—($C_{1-30}$ alkyl ether, $C_{6-40}$ aryl ether, $C_{7-2000}$ alklaryl ether, or $C_{7-2000}$ arylalkyl ether)$^{1-100}$—CO—NH—($R^b$ or Ar—$R^b$—Ar)—NH—CO—O—, —$R^a$—O—CO—NH—($R^b$ or Ar—$R^b$—Ar)—NH—CO—O—($C_{2-50}$ alkyl ester, $C_{7-60}$ aryl ester, $C_{8-2000}$ alkylaryl ester, or $C_{8-2000}$ arylalkyl ester)$_{1-100}$—$R^c$—O—CO—NH—($R^b$ or $Ar$—$R^b$—Ar)—NH—CO—O—, —$R^a$—NH—CO—NH—($R^b$ or Ar—$R^b$—Ar)—NH—CO—O—($C_{1-30}$ alkyl ether, $C_{6-40}$ aryl ether, $C_{7-2000}$ alkylaryl ether, or $C_{7-2000}$ arylalkyl ether)$_{1-100}$, —$R^a$—NH—CO—NH —($R^b$ or Ar—$R^b$—Ar)—NH—CO—O—($C_{2-50}$ alkyl ester, $C_{7-60}$ aryl ester, $C_{8-2000}$ alkylaryl ester, or $C_{8-2000}$ arylalkyl ester)$_{1-100}$, —$R^a$—NH—CO—NH—($R^b$ or Ar—$R^b$—Ar)—NH—CO—O—($C_{1-30}$ alkyl ether, $C_{6-40}$ aryl ether, $C_{7-2000}$ alkylaryl ether, or $C_{7-2000}$ arylalkyl ether)$_{1-100}$—CO—NH—($R^b$ or Ar—$R^b$—Ar)—NH—CO—O—, —$R^a$—NH—CO—NH—($R^b$ or Ar—$R^b$—Ar)—NH—CO—O—($C_{2-50}$ alkyl ester, $C_{7-60}$ aryl ester, $C_{8-2000}$ alkylaryl ester, or $C_{8-2000}$ arylalkyl ester)$^{1-100}$—$R^c$—O—CO—NH—($R^b$ or Ar—$R^b$—Ar)—NH—CO—O—, —$R^a$—O—CO—NH—($R^b$ or Ar—$R^b$—Ar)—NH—CO—NH—($C_{2-50}$ alkyl amide, $C_{7-60}$ aryl amide, $C_{8-2000}$ alkylaryl amide, or $C_{8-2000}$ arylalkyl amide)$_{1-100}$, or —$R^a$—NH—CO—NH—($R^b$ or Ar—$R^b$—Ar)—NH—CO—NH—($C_{2-50}$ alkyl amide, $C_{7-60}$ aryl amide $C_{8-2000}$ alkylaryl amide, or $C_{8-2000}$ arylalkyl amide)$_{1-100}$; and each Z, independently, is —H or —G—D, wherein G is —$R^a$—, —$R^a$—Ar—, —Ar—$R^a$—, or —Ar—; and D is —H, —OH, —SH, —NH$_2$, —NHOH, —SO$_3$H, —OSO$_3$H, —CO$_2$H, —CONH$_2$, —CONHNH$_2$, —CH(NH$_2$)—CO$_2$H, —NH—CH$_2$—CO$_2$H, —P(OH)$_3$, —PO(OH)$_2$, —O—PO(OH)$_2$, —O—PO(OH)—O—PO(OH)$_2$, —O—PO(O$^-$)—O—CH$_2$CH$_2$NH$_3^+$, —O—PO(O$^{31}$)—O—CH$_2$CH$_2$—N$^+$(CH$_3$)$_3$, -glycoside, -oligosaccharide, —CO-glycoside, —CO-oligosaccharide, —OCH$_3$, —OCH$_2$(CHOH)$_4$—CH$_2$OH, —OCH$_2$(CHOH)$_2$—CH$_2$OH, —CO—OCH$_2$(CHOH)$_4$—CH$_2$OH, —C$_6$H$_3$(OH)$_2$, —N(CH$_2$CO$_2$H)$_2$, —CO—N(CH$_2$CO$_2$H)$_2$, —CO—NH—C(CH$_2$CH$_2$CO$_2$H)$_3$, —CO-NH-C(CH$_2$CH$_2$OH)$_3$, —[CH$_2$—CH(CO$_2$R$^a$)]$_{1-100}$—H, —NH$_3^+$,—N$^+$H$_2$R$^a$, —N$^+$HR$^a$R$^b$, or —N$^+$R$^a$R$^b$R$^c$, each of R$^a$, R$^b$, and R$^c$, independently, being $C_{1-20}$ linear or branched alkyl, and Ar being aryl; R is alkyl, hydroxy, or amino; W is O, C(CN)$_2$, N$^+$Y$_1$Y$_2$, or V; V is $C_{5-20}$ aryl, $C_{2-20}$ heteroaryl, $C_{1-20}$ alkylamino, $C_{1-20}$ alkoxy, or $C_{1-20}$ alkylthiol; n is 1–10; p is 0–20; q is 0–20; and r is 0 or 1. Referring to (—E)$_p$ in formula (I), if p is two or greater and two or more $Y_1$'s are respectively assigned to the E's, the $Y_1$'s can be the same or different. The same rule applies to similar situations.

By the term "alkyl" is meant a straight-chain or branched hydrocarbon. An alkyl group may also contain one or more double bond or triple bond and the cyclic alkyl groups may contain one or more heteroatoms, which are, typically, nitrogen, oxygen, or sulfur. Examples of an alkyl group include, but are not limited to, methyl, ethyl, propyl, isopropyl, butyl, isobutyl, tert-butyl, amyl, pentyl, hexyl, heptyl, octyl, nonyl, decyl, pentadecyl, icosyl, allyl, 2-butenyl, 2-pentenyl, 3-hexenyl, 4-decenyl, 5-nonadecenyl, 2-butnyl, 3-octnyl, 5-octadecnyl, cyclopropyl, cyclopentyl, cyclohexyl, cycloheptyl, adamantyl, norbornyl, isobornyl, cyclopentyl-methyl, cyclohexylmethyl, 1- or 2-cyclohexylethyl, cyclo-pentenyl, cyclohexenyl, cycloheptenyl, cyclo-octenyl, tetra-hydrofuranyl, tetrahydropyranyl, piperidinyl, morpholino and pyrrolindinyl groups.

As used herein, the term "aryl" refers to aromatic rings. These moieties may be fused rings and may be fused with aryl or heteroaryl as defined below. Fused rings are rings that share a common carbon-carbon bond. Typically aryl groups include phenyl, naphthyl, biphenyl, indazolyl, phenanthryl, and anthracyl.

By the term "heteroaryl" is meant an aromatic ring that contains one or more heteroatoms as defined above. It may be a fused ring. Examples of heteroaryl groups include pyridyl, pyrazinyl, pyrimidyl, furyl, pyrrolyl, thienyl, thiazolyl, oxazolyl, imidazolyl, coumarinyl, indolyl, benzofuranyl, benzthiazolyl, benzothienyl, and benzothiadiazolyl.

As used herein, the term "halo" include fluoro, chloro, bromo, and iodo.

The compounds include their pharmaceutically acceptable salts, if applicable. Such a salt can be formed between a positively charged substituent (e.g., amino) in a fused pyrazolyl compound and a negatively charged counterion (e.g., chloride, bromide, iodide, sulfate, nitrate, phosphate, or acetate). Likewise, a negatively charged substituent (e.g., carboxylate) in a fused pyrazolyl compound can form a salt with a positively charged ion (e.g., sodium ion, potassium ion, magnesium ion, calcium ion, or an ammonium cation such as tetramethylammonium ion).

Subsets of the above-described compounds include those in which F is a fullerene core of $C_{60}$, $C_{70}$, $C_{76}$, $C_{78}$, $C_{82}$, $C_{84}$, $C_{92}$ (methano)$_n$C$_{60}$, (pyrrolidino)$_n$C$_{60}$La@C$_s$, Ho@C$_s$, Gd@C$_s$, or Er@C$_s$, n is 1–10, and s is 60, 74, or 82; those in which each of $X_1$, $X_2$, $X_3$, $X_4$, and $X_5$, independently, is hydrogen; those in which each of $Y_1$, $Y_2$, and $Y_3$, independently, is hydrogen, $C_{1-2000}$ alkyl, $C_{6-40}$ aryl, or $C_{7-2000}$ arylalkyl, optioanlly substituted with —OH, —SH, —NH$_2$, —NHOH, —SO$_3$H, —OSO$_3$H, —CO$_2$H, —CONH$_2$, —CONHNH$_2$, —CH(NH$_2$)—CO$_2$H, —NH—CH$_2$—CO$_2$H, —NH$_3^+$, —N$^+$H$_2$R$^a$, —N$^+$HR$^a$R$^b$, or —N$^+$R$^a$R$^b$R$^c$ (e.g., ethyl, hydroxyethyl, methoxyethyl, solfonylbutoxyethyl, hydroxycarbonylmethyl, or hydroxycarbonylethyl); those in which r is 0; those in which r is 1, and V is aryl (e.g., phenyl); those in which E is $Y_1$,$Y_2$-amino (e.g., diphenylamino), $Y_2$-amino, ($Y_1$, $Y_2$-alkyl)-amino, $Y_1$, $Y_2$-ethylenediamino, (dihydroxymethyl)alkylamino, ($X_1$, $X_3$-aryl) amino, ($Y_1$,$Y_2$,$Y_3$-alkyl)amino, ($Y_1$,$Y_2$, $Y_3$-aryl)amino, dihydroxyalkylamino, (trihydroxyalkyl)alkylamino, or (dicarboxyalkyl)amino; p is 1–4; and those in which R is hydroxy or amino. Additional subsets include compounds in which W is O, C(CN)$_2$, heteroaryl, N$^+$Y$_1$Y$_2$, each of $Y_1$ and $Y_2$, independently, being hydrogen, alkyl, aryl, or heteroaryl, or, together being aryl or heteroaryl. Additional examples of W include the following groups:

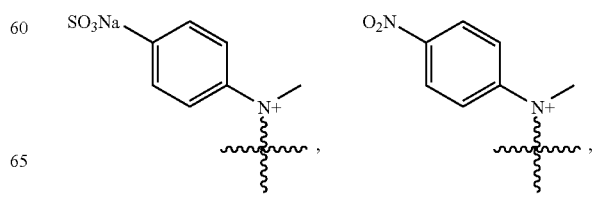

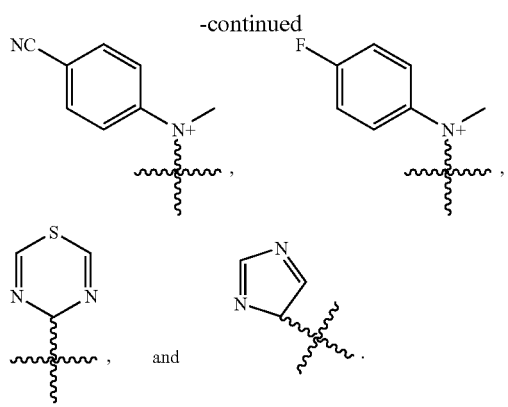
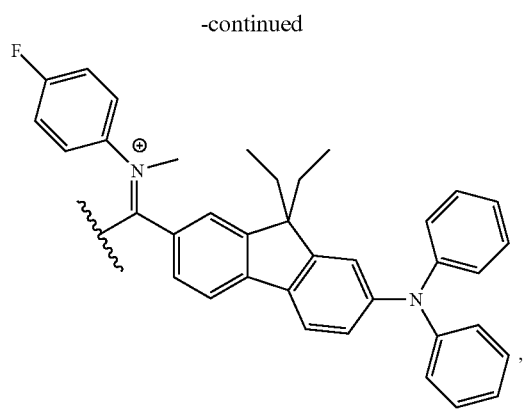
Examples of the compounds of this invention include those of the formula F(—M)$_n$, in which F is a fullerene core of $C_{60}$, n is 1–6, each M, independently, is of one of the following formulae:
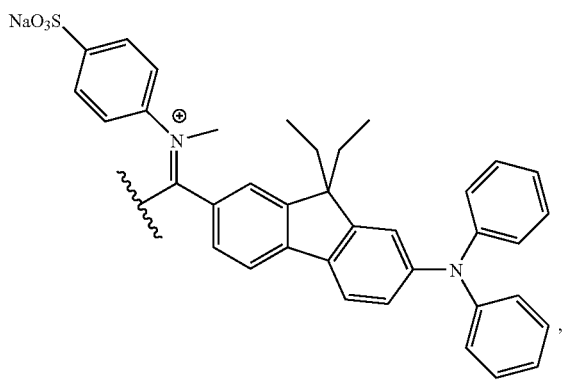
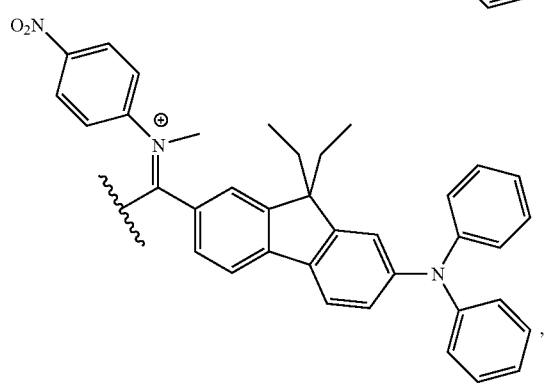
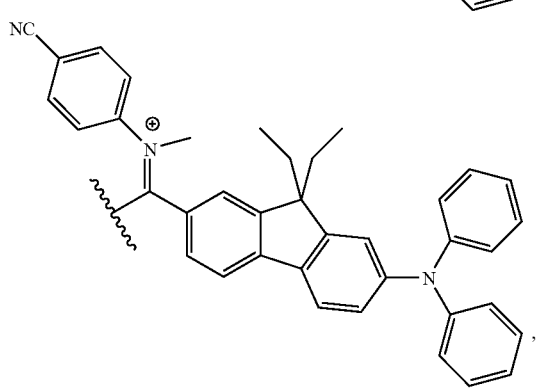
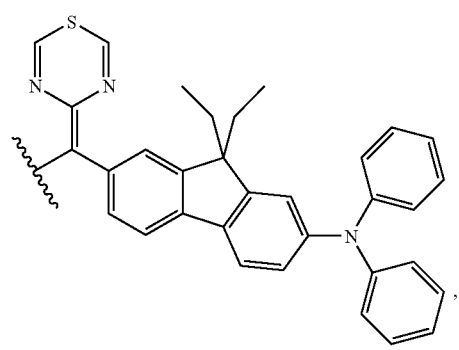
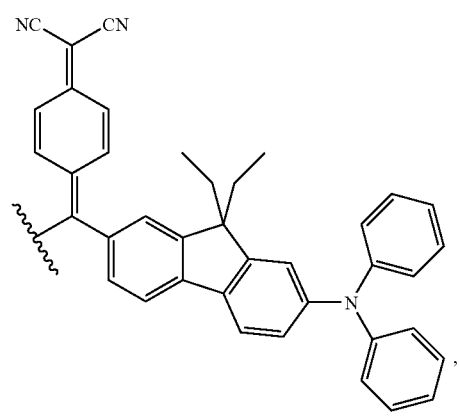
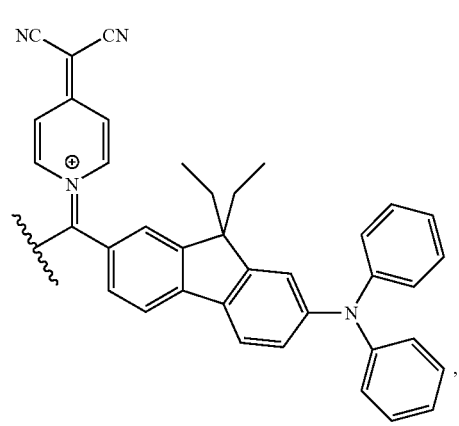

-continued
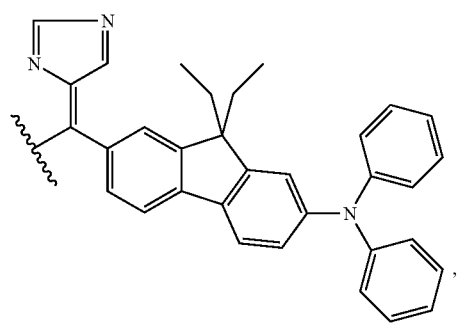
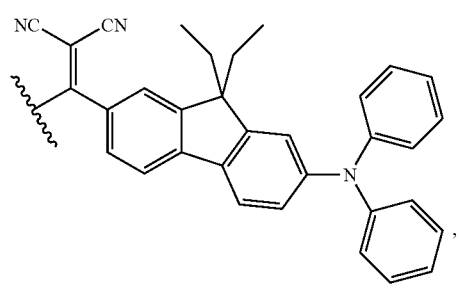
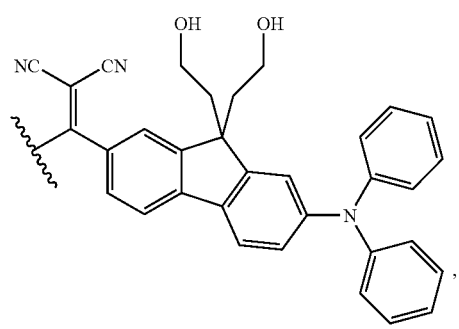
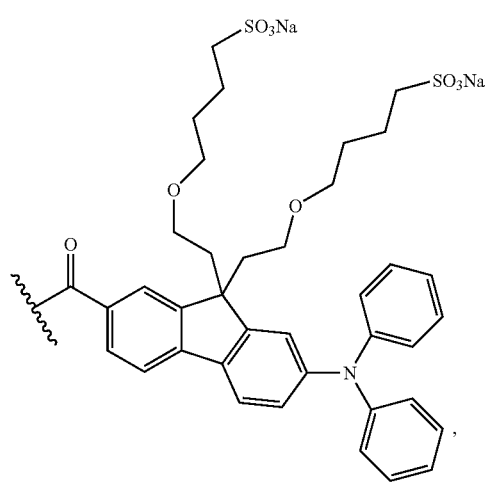
-continued
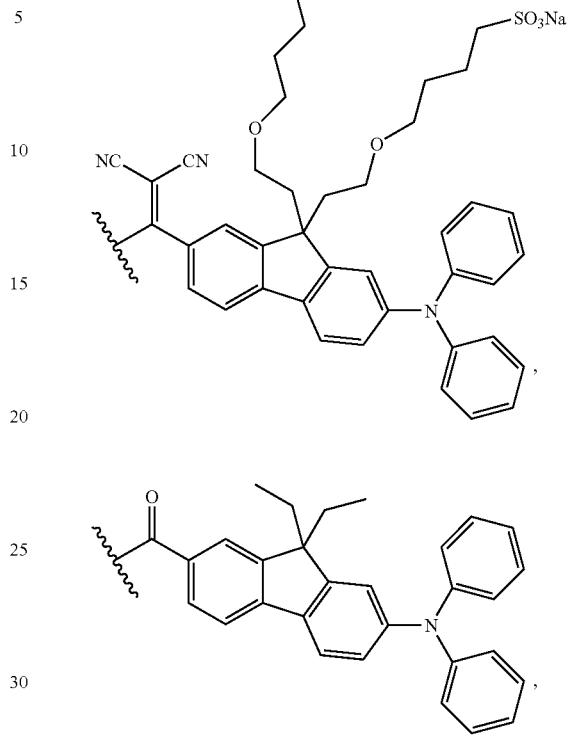
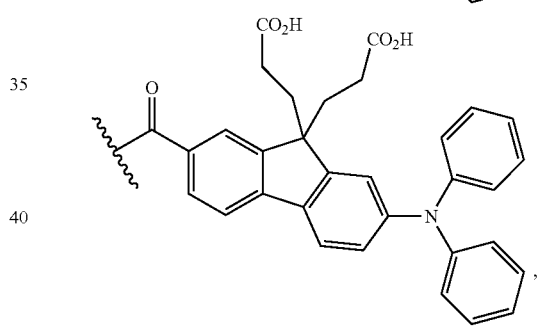
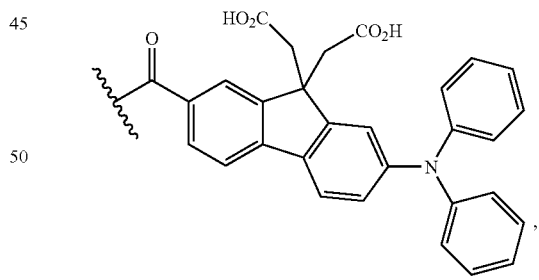
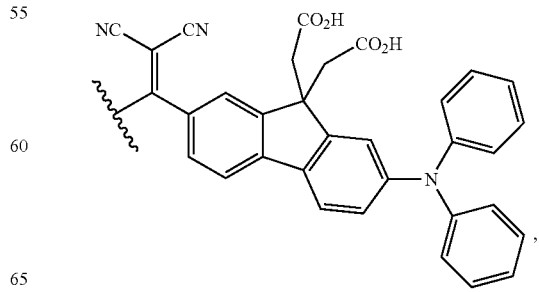

-continued

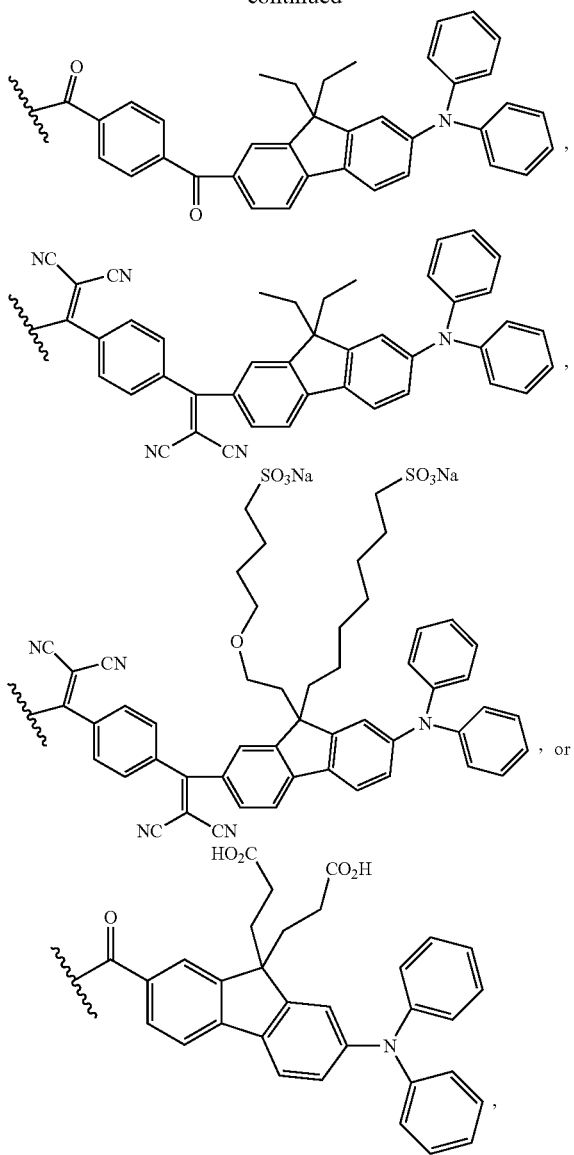

The fullerene compounds of this invention, under irradiation, they can generate free radicals, such as $O_2^-$, which are cytotoxic to tumor cells. Thus, they can be used in inhibiting the growth (including causing the death) of tumor cells. Accordingly, the invention also relates to pharmaceutically acceptable compositions each including a pharmaceutical carrier and one or more of the above-described compound.

Also within the scope of this invention is a method of inhibiting the growth, including causing the death, of tumor cells. The method includes administering to a tumor site of a subject in need thereof a compound or composition described above and, subsequently, exposing the tumor site to irradiation.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of several compounds of the invention are set forth in the accompanying drawings and the description below. Other features, objects, and advantages of the invention will be apparent from the description and drawings, and from the claims.

DETAILED DESCRIPTION OF THE INVENTION

The compounds of this invention can be synthesized by methods known in the art. Scheme 1 below shows the syntheiss of a compound of this invention:

Scheme 1 Reagents and conditions: i, iodoethane, NaOH, tetrabutylamino bromide, toluene, 60° C., h; ii, diphenylamine (1.0 equiv.), tris(dibenzylideneacetone)dipalladium(0) (cat.), rac-BINAP, sodium t-butoxide, toluene, 110° C., 8 h; iii, bromoacetyl bromide, $AlCl_3$, $CH_2CH_2$, 0° C. to r.t., 4 h; iv, $C_{60}$, 1,8-diazabicyclo[5.4.0]undec-7-ene, toluene, room temperature, 5 h.

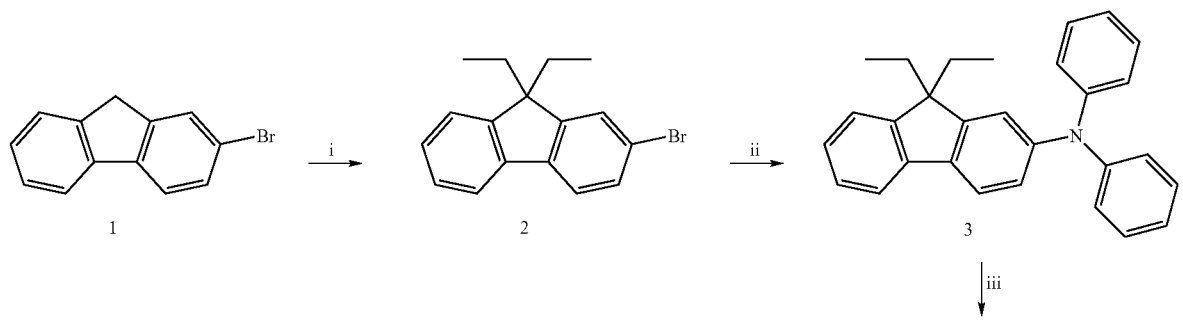

-continued

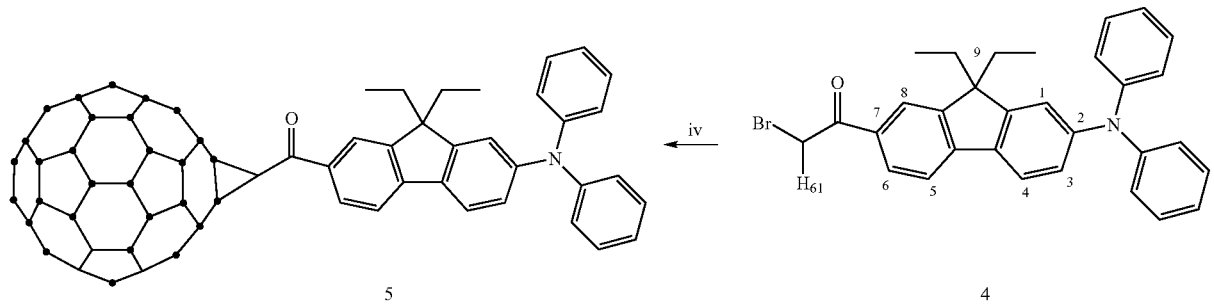

Referring to Scheme 1 above, 2-bromofluorene 1 is used to prepare a diethyl-2-diphenylaminofluorene 2, which is then reacted, under catalytic condensation conditions, with an amino (e.g., diphenylamine) to obtain an amino-substituted diethyl-2-diphenylaminofluorene 3. Friedel-Crafts condensation of 3 with a mixture of bromoacetyl bromide and aluminum chloride in 1,2-dichloroethane gives a bromoacetyl amino-substituted fluorene compound 4. The reaction of a fullerene compound with 4 in toluene gives a desired compound of this invention.

Referring to formula (I), additional substitutents (when n is greater than 1) can be introduced by using a greater amount of compound 4. The fullerene compounds of this invention in which W is $C(CN)_2$, $N^+Y_1Y_2$, aryl, or heteroaryl can be prepared by reacting the compound (or other compounds having a carbonyl group, i.e., in which W is O) with reagents such as dicyanomethane, substituted hydrazine or amine; or by using reagents containing aryl (e.g., phenyl) or heteroaryl (e.g., pyridynyl) as W, instead of bromoacetyl bromide. See, e.g., March, Advanced Organic Chemistry (Reactions, Mechanisms, and Structure), $4^{th}$ Edition, John, Wiley & Sons, New York, 1992. The fullerene compounds of this invention in which r is 1 can be prepared by coupling compound 3 with dihalogenated aryl or heteroaryl, and then subjecting the product of the coupling reaction to the Friedel-Crafts condensation shown in Scheme 1. Substituents on a fullerene core, such as various R and E shown above, can be introduced by methods described in U.S. Pat. Nos. 6,020,523, 6,046,361, and 6,380, 434. Different $X_1$, $X_2$, $X_3$, $X_4$, $X_5$, $Y_1$, and $Y_2$ can be introduced by using starting materials that are pre-substituted with desired groups (e.g., each of $X_1$, $X_2$, $X_3$, and $X_4$, independently, is methyl; and $X_5$ is chloro).

A compound of this invention or its salt in a sufficient amount is formulated with a pharmaceutically acceptable carrier to form a pharmaceutical composition before being administered to a subject in need of treatment of a tumor. "A sufficient amount" refers to the amount of the compound which is required to confer therapeutic effect on the treated subject. The interrelationship of dosages for animals and humans (based on milligrams per meter squared of body surface) is described by Freireich et al., Cancer Chemother. Rep., 1966, 50, 219. Body surface area may be approximately determined from height and weight of the patient. See, e.g., Scientific Tables, Geigy Pharmaceuticals, Ardley, N.Y., 1970, 537. Effective doses will also vary, as recognized by those skilled in the art, depending on the route of administration, the excipient usage, the distance of tumor from the skin surface, the source of the irradiation, and the optional co-usage with other therapeutic treatments including use of other anti-tumor compounds.

The pharmaceutical composition may be administered via a parenteral route, e.g., topically, intraperitoneally, and intravenously. Examples of parenteral dosage forms include an active compound dissolved in phosphate buffer solution (PBS), or admixed with any other pharmaceutically acceptable carrier. Solubilizing agents, such as cyclodextrins, or other solubilizing agents well known to those familiar with the art, can also be included in the pharmaceutical composition.

An in vitro inhibition assay can be used to preliminarily evaluate a fullerene compound's ability to inhibit the growth of tumor cells. For example, a fullerene compound solution can be added to a pre-incubated cell suspension. Subsequently, the cell suspension is irradiated with fluorescence light, followed by further incubation. A solution of 3-(4,5-dimethylthiazol-2-yl)-2,5-diphenyl-tetrazolium bromide is added to the cell suspension to react with mitochrondrial dehydrogenase to form formazon, which is extracted with dimethyl sulfoxide (DMSO). The DMSO extract is immediately used for optical measurement to determine the quantity of formazon, which correlates with the quantity of dehydrogenase or the relative number of the living cells.

The fullerene compounds that have been preliminarily evaluated can be further tested to confirm their efficacy by an in vivo inhibition assay. See Chiang, et al., *Proc. Electrochem. Soc.*, 1999, 99-12, 238–249, and U.S. application Ser. No. 09/666,989. For example, a tumor-bearing mouse can be first administered a suitable fullerene compound in PBS close to the tumor site. The mouse is then kept in the dark while the fullerene compound is circulated to the tumor site. After the hair on and around the tumor site is removed, the tumor site is irradiated with a laser beam or other light source. After the irradiation, the growth of the tumor in the mouse is examined at different intervals. The inhibitory effect is evaluated by measuring the mouse's average body weight and tumor volume. The mouse is euthanatized by carbon dioxide asphyxiation. The final body weight and organ weight of the treated mouse are measured. Blood samples are withdrawn for biochemistry and hematology analyses. All such data can be used to evaluate the efficacy of the fullerene compound to treat tumor.

Without further elaboration, it is believed that one skilled in the art, based on the description herein, can utilize the present invention to its fullest extent. The following specific examples, which describe synthesis and biological testing of several compounds of this present invention, are therefore to be construed as merely illustrative, and not limitative of the remainder of the disclosure in any way whatsoever.

EXAMPLE 1

Synthesis of 2-bromo-9,9-diethylfluorene

To a solution of 2-bromofluorene (2.5 g, 10 mmol) in toluene (40 ml) was added tetrabutylammonium bromide (0.8 g, 2.48 mmol) as a phase transfer catalyst. A freshly prepared solution of aqueous sodium hydroxide (25 ml, 50% w/w) was added at once to the solution. The mixture turned orange and became viscous. To this solution, iodoethane (2.4 ml, 30 mmol) was added. The mixture was stirred at 60° C. for a period of 8 h. It was diluted with ethyl acetate (25 ml) and washed several portions of water. Organic layer was dried over magnesium sulfate and concentrated in vacuuo to afford the crude product liquid. The products were purified by column chromatography (silica gel, hexane as eluent, $R_f$=0.8 on thin layer chromatography) giving colorless oil of 2-bromo-9,9-diethylfluorene (2.5 g) in a yield of 82%.

$^1$H NMR (CDCl$_3$) δ 0.24 (t, J=8 Hz, 6H), 1.94–1.91 (m, 4H), 7.25–7.23 (m, 3H), 7.38–7.36 (m, 2H), 7.49–7.46 (m, 1H), and 7.61–7.59 (m, 1H).

EXAMPLE 2

Synthesis of 9,9-diethyl-2-diphenylaminofluorene

A mixture of 2-bromo-9,9-diethylfluorene (2.44 g, 8.10 mmol), diphenylamine (1.43 g, 8.5 mmol), tris(dibenzylideneacetone)dipalladium (0.018 g, 0.25 mmol %), rac-BINAP (0.037 g, 0.75 mmol %), and sodium t-butoxide (1.08 g, 11.34 mmol) in dry toluene (100 ml) was heated at the refluxing temperature of the solvent for 8–10 h under an atmospheric pressure of nitrogen. After cooling the reaction mixture to room temperature, it was diluted with diethylether (60 ml), washed with brine (40 ml) and water. Organic layer was dried over sodium sulfate and concentrated in vacuuo. The crude product was purified by column chromatography (silica gel, hexane-toluene/9:1 as eluent, $R_f$=0.6 on thin layer chromatography using hexane-toluene/4:1 as eluent) to give 9,9-diethyl-2-diphenylaminofluorene (3.1 g) as a white amorphous low melting solid in a yield of 98%.

$^1$H NMR (CDCl$_3$) δ 0.36 (t, J=7.3 Hz, 6H), 1.99–1.87 (m, 4H), 7.06–6.99 (m, 3H), 7.15–7.12 (m, 5H), 7.33–7.23 (m, 7H), and 7.64–7.57 (m, 2H).

EXAMPLE 3

Synthesis of 7-bromoacetyl-9,9-diethyl-2-diphenylaminofluorene

To a suspension of aluminium chloride (0.375 g, 2.82 mmol) in 1,2-dichloroethane (15 ml) at 0° C. was added a solution of 2-diphenylamino-9,9-diethylfluorene (1.0 g, 2.57 mmol) in 1,2-dichloroethane (15 ml). Bromoacetyl bromide (0.269 ml, 3.08 mmol) was added over a period of 10 min to maintain a steady reaction temperature between 0–10° C. under an ice-bath. At the end of addition, the mixture was warmed to ambient temperature, stirred for another 4 h, and quenched by a slow addition of water (50 ml) to maintain the mixture temperature below 45° C. Organic layer was washed subsequently with dil. HCl (1.0 N, 50 ml) and water (50 ml, twice). It was concentrated in vacuuo to give crystalline yellow solids. These crude products were purified by column chromatography (silica gel, hexane-toluene/3:2 as eluent, $R_f$=0.3 on thin layer chromatography using the same solvent mixture as eluent) to afford 7-bromoacetyl-9,9-diethyl-2-diphenylaminofluorene (0.87 g) as yellow crystalline solids in a yield of 66%

IR (KBr) $v_{max}$ 3037, 2966, 2928, 2878, 1674,1595, 1491, 1281, 754, and 698 cm$^{-1}$. $^1$H NMR (CDCl$_3$) δ 0.35 (t, J=7.3 Hz, 6H), 2.05–1.84 (m, 4H), 4.49 (s, 2H), 7.05–7.02 (m, 2H), 7.28–7.09 (m 10H), 7.60 (d, J=8 Hz, 1H), 7.65 (d, J=8 Hz, 1H), 7.92 (d, 1H), and 7.95 (dd, 1H). $^{13}$C NMR (CDCl$_3$) δ 8.47, 31.15, 32.36, 56.22, 118.10, 118.77, 121.59, 122.80, 123.10, 124.40, 128.87, 129.21, 129.27, 131.56, 134.26, 147.26, 147.60, 148.88, 150.28, 152.81, and 191.04.

EXAMPLE 4

Synthesis of 7-(1,2-dihydro-1,2-methano[60]fullerene-61-carbonyl)-9,9-diethyl-2-diphenylaminofluorene To a mixture of C$_{60}$ (1.0 g, 1.38 mmol) and 7-bromoacetyl-9,9-diethyl-2-diphenylaminofluorene (0.7 g, 1.38 mmol) in toluene (700 ml) was added 1,8-diazabicyclo[5.4.0]undec-7-ene (DBU, 0.205 ml, 1.38 mmol) under atmospheric pressure of nitrogen. After stirring at room temperature for a period of 5 h under N$_2$, the reaction mixture was filtered, concentrated to 10% of the original volume. Crude products were precipitated by addition of methanol and isolated by centrifugation. It was further purified by column chromatography (silica gel, hexane-toluene/3:2 as eluent, $R_f$=0.6 on thin layer chromatography using the same solvent mixture as eluent) to afford greenish brown solids of 7-(1,2-dihydro-1,2-methano[60]fullerene-61-carbonyl)-9,9-diethyl-2-diphenylaminofluorene (0.78 g) in a yield of 71% after taking recovered C$_{60}$ into account.

IR (KBr) $υ_{max}$ 3029, 2963, 2921, 1677, 1591, 1492, 1276, 750, 695, and 524 cm$^{-1}$. $^1$H NMR (CDCl$_3$) δ 0.40 (t, J=8 Hz, 6H), 2.13-1.89 (m, 4H), 5.69 (s, 1H), 7.07–7.03 (m 2H), 7.29–7.11 (m, 10H), 7.66 (d, J=8 Hz, 1H), 7.83 (d, J=8 Hz, 1H), 8.32 (d, J=1.6, Hz, 1H), and 8.48 (dd, J=8 Hz, 1.6 Hz, 1H). $^{13}$C NMR (CDCl$_3$) δ 8.66, 32.53, 44.38, 56.41, 72.65, 118.09, 119.20, 121.83, 122.83, 123.07, 123.23, 124.53, 128.95, 129.34, 133.50, 134.19, 136.61, 139.69, 140.92, 141.20, 142.07, 142.19, 142.23, 142.48, 142.75, 142.94, 142.95, 143.00, 143.14, 143.31, 143.68, 143.93, 144.30, 144.59, 144.63, 144.70, 144.86, 145.03, 145.14, 145.25, 145.39, 145.60, 146.89, 147.62, 147.90, 148.24, 149.13, 150.78, 153.03, and 189.56. Single crystal x-ray data: C$_{91}$H$_{27}$NO, 1150.14 (M), monoclinic, P2$_1$/n, T=295 (2) K, a=10.00100 (10) Å, b=19.5790 (2) Å, c=25.7150 (3) Å, α=90°, β=93.0510 (10)°, γ=90°, V=5028.11 (9) Å$^3$, Z=4, $R_{int}$=0.0396, abs. coefficient 0.089 mm$^{-1}$, $R_1$=0.0524 and wR$_2$=0.1279 for I>2σ (I).

EXAMPLE 5

Synthesis of 7-(1,2-dihydro-1,2-methano[60]fullerene-61-(1,1-dicyanoethylene))-9,9-diethyl-2-diphenylaminofluorene A reaction flask containing a solution of 7-(1,2-dihydro-1,2-methano[60]fullerene-61-carbonyl)-9,9-diethyl-2-diphenylaminofluorine (0.3 g, 0.261 mmol) and malanonitrile (0.034 g, 0.52 mmol) in dry toluene (25 ml) under atmospheric pressure of nitrogen was added pyridine (0.082 g, 1.04 mmol) with stirring. To this mixture, excessive titanium tetrachloride was added. After stirring at room temperature for a period of 5 min, the reaction mixture was quenched with water (30 ml). Organic layer was washed several times with water, dried over magnesium sulfate, and concentrated in vacuuo to give orange-red solids. The crude solid products were further purified by preparative thin layer chromatography (TLC, silica gel, $R_f$=0.3 using hexane-toluene/3:2 as eluent) to afford 7-(1,2-dihydro-1,2-methano[60]fullerene-61-(1,1-dicyanoethylene))-9,9-diethyl-2-diphenylaminofluorene as orange red solids (0.2 g) in a yield of 67%.

IR (KBr) $v_{max}$ 3033, 2963, 2923, 2875, 2224, 1592, 1492, 1278, 750, 697, and 524 cm$^{-1}$. $^1$H NMR (CDCl$_3$) δ 0.29 (t, J=7.2 Hz, 6H), 2.05-1.88 (m, 4H), 5.52 (s, 1H), 7.27–7.08 (m, 10H), 7.58 (d, J=8 Hz, 1H), 7.78 (d, J=8 Hz, 1H), 7.99 (d, 1 $^{13}$C NMR (CDCl$_3$) δ 8.60, 32.61, 41.34, 56.58, 72.46, 87.66, 113.26, 113.30, 168.83, 117.68, 119.75, 121.87, 122.67, 122.99, 123.38, 124.61, 128.24, 129.35, 132.15, 133.76, 137.06, 137.45, 141.04, 141.04, 141.42, 141.95, 141.04, 141.42, 141.95, 142.05, 142.45, 142.98, 143.76, 143.80, 144.26, 144.50, 144.66, 144.77, 144.81, 145.09, 145.24, 145.28, 145.30, 145.36, 145.83, 147.41, 147.45, 149.43, 150.92, 152.66, and 168.83. Single crystal x-ray data: $C_{98.25}H_{36}N_3O_{1.5}S_{0.25}$, 1290.32 (M), monoclinic, P2(1)/c, T=295 (2) K, a=22.0080 (2) Å, b=9.98300 (10) Å, c=28.1780 (3) Å, α=90°, β=93.4330(10)°, γ=90°, V=6179.76 (11) Å$^3$, Z=4, abs. coefficient 0.090 mm$^{-1}$, $R_1$=0.0831 and $wR_2$=0.1932 for I>2σ(I).

EXAMPLE 6

Synthesis of 2-bromo-9,9-dimethoxyethylfluorene (Method 1)

To a solution of 2-bromofluorene (2.0 g, 8.2 mmol) in dimethylformamide (dry, 30 ml) was added potassium t-butoxide (2.74 g, 24.4 mmol), giving a deep orange in color. The mixture was stirred at 45° C. for 20 min and added 2-bromoethylmethyl ether (3.5 g, 2.5 mmol) dropwise. Stirring was continued at the same temperature for overnight to give an orange solution. Another portion of 2-bromoethyl-methyl ether (1.4 g, 1.0 mmol) was added and the mixture stirred at 80° C. for 4 h. It was diluted with water (100 ml). The products extracted with ethylacetate (20 ml) and washed with water. Organic layer was dried over magnesium sulfate and concentrated in vacuuo to afford the crude product. It was purified by preparative thin layer chromatography (silica gel, $R_f$=0.3 using hexane-EtOAc/3:2 as eluent) to give 2-bromo-9,9-dimethoxyethylfluorene (1.5 g).

$^1$H NMR (CDCl$_3$) δ 2.37–2.27 (m, 4H), 2.70–2.63 (m, 4H), 3.00 (s, 6H), 7.36–7.32 (m, 2H),

EXAMPLE 7

Synthesis of 2-bromo-9,9-dimethoxyethylfluorene (Method 2)

To a solution of 2-bromofluorene (2.45 g, 10 mmol) in tetrahydrofuran (dry, 75 ml) was added potassium t-butoxide (3.36 g, 30 mmol), giving a deep orange solution. The mixture was stirred at ambient temperature for 10 min and added 2-methoxyethyl mesylate in tetrahydrofuran dropwise. Exothermic reaction was observed. Stirring was continued at ambient temperature for overnight to give an orange solution. At the end of the reaction, it was diluted with water (150 ml). The products extracted with ethylacetate (30 ml) and washed with water. Organic layer was dried over magnesium sulfate and concentrated in vacuuo to afford the crude product. It was purified by preparative thin layer chromatography (silica gel, $R_f$=0.3 using hexane-EtOAc/3:2 as eluent) to give 2-bromo-9,9-dimethoxyethylfluorene (3.3 g).

EXAMPLE 8

Synthesis of 9,9-dimethoxyethyl-2-diphenylaminofluorene

In a round-bottom flask, a mixture of 2-bromo-9,9-dimethoxyethylfluorene (2.0 g, 5.54 mmol), diphenylamine (1.12 g, 6.65 mmol), tris(dibenzylideneacetone)dipalladium (0) (0.012 g, 0.25 mmol %), rac-BINAP (0.025 g, 0.75 mmol %), and sodium t-butoxide (0.74 g, 7.76 mmol) in dry toluene (100 ml) was placed and heated at the refluxing temperature of the solvent for 16 h under an atmospheric pressure of nitrogen. After cooling the reaction mixture to room temperature, it was diluted with diethylether (60 ml), washed with brine (40 ml) and water. Organic layer was dried over sodium sulfate and concentrated in vacuuo. The crude product was purified by preparative thin layer chromatography (silica gel, $R_f$=0.3 using hexane-EtOAc-toluene/1:1:3 as eluent) to give 9,9-dimethoxyethyl-2-diphenylaminofluorene (1.6 g).

$^1$H NMR (CDCl$_3$) δ 2.32–2.23 (m, 4H), 2.86–2.71 (m, 4H), 3.07 (s, 6H), 7.06–7.02 (m, 2H), 7.17–7.06 (m, 5H), 7.44–7.23 (m, 8H), and 7.64–7.57 (m, 2H). $^{13}$C NMR (CDCl$_3$δ39.22, 50.95, 58.19, 68.56, 119.14, 119.17, 120.43, 122.64, 122.72, 123.57, 123.88, 126.53, 127.26, 129.12, 135.17, 140.10, 147.39, 147.77, 148.82, and 150.16.

EXAMPLE 9

Synthesis of 7-bromoacetyl-9,9-dimethoxyethyl-2-diphenylaminofluorene

To a suspension of aluminium chloride (0.49 g, 3.67 mmol) in 1,2-dichloroethane (20 ml) at 0° C. was added a solution of 2-diphenylamino-9,9-dimethoxyethylfluorene (1.5 g, 3.34 mmol) in 1,2-dichloroethane (15 ml) and the mixture stirred for 10 min. Bromoacetyl bromide (0.8 g, 4.0 mmol) was added over a period of 10 min to maintain a steady reaction temperature between 0–25° C. under a cool water-bath. At the end of addition, the mixture was warmed to ambient temperature and stirred for another 16 h. The solution was diluted by a slow addition of water (50 ml) to maintain the mixture temperature below 30° C. Organic layer was washed subsequently with dil. HCl (1.0 N, 50 ml), water (50 ml, twice), dried over MgSO$_4$, and concentrated in vacuuo to give bright yellow solids. These crude products were purified by preparative thin layer chromatography (silica gel, $R_f$=0.8 using hexane-EtOAc/3:2 as eluent) to afford 7-bromoacetyl-9,9-dimethoxyethyl-2-diphenylaminofluorene (0.6 g) as yellow crystalline solids.

$^1$H NMR (CDCl$_3$) δ 2.30–2.20 (m, 4H), 2.30–2.20 (m, 4H), 2.78–2.72 (m, 4H), 3.01 (s, 6H), 4.47 (s, 2H), 7.06–7.04 (m, 2H), 7.28–7.10 (m, 10H), 7.57 (d, J=8 Hz, 1H), and 8.02–7.95 (m, 2H). $^{13}$C NMR (CDCl$_3$) δ 31.00, 38.99, 51.34, 58.32, 68.49, 117.95, 119.02, 121.76, 122.77, 123.42, 124.64, 124.64, 129.22, 129.36, 131.73, 132.84, 146.12, 147.43, 149.15, 149.45, 149.45, 151.94, and 190.87.

EXAMPLE 10

Synthesis of 7-(1,2-dihydro-1,2-methano[60]fullerene-61-carbonyl)-9,9-dimethoxyethyl-2-diphenylaminofluorene To a mixture of C$_{60}$ (0.74 g, 1.05 mmol) and 7-bromoacetyl-9,9-dimethoxyethyl-2-diphenylaminofluorene (0.6 g, 1.05 mmol) in toluene (dry, 400 ml) was added 1,8-diazabicyclo[5.4.0]undec-7-ene (DBU, 0.165 g, 1.05 mmol) under atmospheric pressure of nitrogen. After stirring at room temperature for a period of 4 h under $N_2$, the reaction mixture was concentrated to a volume of 10 ml. Crude products were precipitated by addition of methanol and isolated by centrifugation. It was further purified by preparative thin layer chromatography (silica gel, $R_f$=0.8 using toluene-EtOAc/9:1 as eluent) to afford greenish brown solids of 7-(1,2-dihydro-1,2-methano[60]fullerene-61-carbonyl)-9,9-dimethoxyethyl-2-diphenylaminofluorene (0.45 g).

$^1$H NMR (CDCl$_3$) δ2.42–2.27 (m, 4H), 2.89–2.82 (m, 4H), 3.05 (s, 6H), 5.71 (s, 1H), 7.12–7.06 (m, 2H), 7.32–7.14 (m, 10H), 7.67 (d, J=8 Hz, 1H), 7.84 (d, J=8 Hz, 1H), 8.45 (d, 1H), and 8.50 (dd, 1H). $^{13}$C NMR (CDCl$_3$) δ 39.19, 44.34, 51.53, 58.44, 68.60, 72.58, 117.96, 119.46, 121.98, 122.81, 123.33, 123.55, 124.75, 129.25, 129.43, 132.79, 133.67, 136.66, 139.64, 140.94, 141.23, 142.09, 142.19, 142.24, 142.50, 142.78, 142.96, 143.01, 143.15, 143.30, 143.70, 143.93, 144.32, 144.62, 144.66, 144.70, 144.86, 145.05, 145.17, 145.26, 145.39, 145.59, 146.72, 146.81, 147.44, 148.15, 148.15, 149.37, 149.98, 152.13, and 189.33.

EXAMPLE 11

Synthesis of 7-(1,2-dihydro-1,2-methano[60]fullerene-61-carbonyl)-9,9-dihydroxyethyl-2-diphenylaminofluorene To a reaction flask was placed 7-(1,2-dihydro-1,2-methano[60]fullerene-61-carbonyl)-9,9-dimethoxyethyl-2-diphenylaminofluorene (0.4 g, 0.33 mmol) and dry dichloromethane (20 ml). A solution of 15-crown-5 (12 equiv., 0.3 M) in $CH_2Cl_2$ saturated with NaI was added. The mixture was stirred and chilled to −30° C. It was then added boron tribromide (BBr$_3$, 6.0 equiv., 0.98 ml, 1.0 M) in $CH_2Cl_2$. The solution was stirred at the same temperature for a period of 3.0 h. After disappearance of the starting material on the thin layer chromatographic plate, the reaction mixture was quenched saturated aqueous NaHCO$_3$ (5.0 ml) and extracted with $CH_2Cl_2$. The organic layer was washed twice with water (40 ml each), dried over sodium sulfate, and concentrated in vacuo. The crude products were further purified by preparative thin layer chromatography (silica gel) to afford solids of 7-(1,2-dihydro-1,2-methano[60]fullerene-61-carbonyl)-9,9-dihydroxyethyl-2-diphenylamino-fluorene (0.3 g).

$^1$H NMR (CDCl$_3$) δ2.26–2.30 (m, 2H), 2.39–2.43 (m, 2H), 3.15 (t, 4H), 5.67 (s, 1H), 7.05–7.13 (m, 6H), 7.24–7.30 (m, 4H), 7.65 (d, J=8 Hz, 1H), 7.82 (d, J=8 Hz, 1H), 8.49 (d, 1H), and 8.51 (dd, 1H).

EXAMPLE 12

Synthesis of Water-Soluble 7-(1,2-dihydro-1,2-methano[60]fullerene-61-carbonyl)-9,9-di(sulfobutoxyethyl)-2diphenylaminofluorene To a reaction flask was placed 7-(1,2-dihydro-1,2-methano [60]fullerene-61-carbonyl)-9,9-dihydroxyethyl-2diphenylaminofluorene (0.14 g, 0.12 mmol) and sodium hydride (0.02 g, 0.46 mmol) in dry tetrahydrofuran (20 ml) under $N_2$. The solution was stirred at ambient temperature for 10 min to dissolve diol. To this solution was added 1,4-butane sultone (0.06 g, 0.46 mmol, 4.0 equiv.). The resulting mixture was stirred at ambient temperature for 15 min and then at 60° C. for a period of 2.0 h. At the end of the reaction, the solvent was evaporated and concentrated to 5.0 ml. Water (distilled, 20 ml) was added to cause precipitation of the products. The solids were separated by centrifuge and washed by acetonitrile (15 ml×4). After drying the solids in vacuum, high water solubility of the products was examined by mixing the solids with a drop of DMSO and then diluted with water. Addition of methanol to the aqueous solution caused precipitation of 7-(1,2-dihydro-1,2-methano [60]fullerene-61-carbonyl)-9,9-di(sulfobutoxyethyl)-2-diphenylaminofluorene (0.15 g).

IR (KBr) $v_{max}$ 3087, 29193, 28503, 1727, 1658, 1588 (s), 1488 (s), 1464, 1426, 1379, 1274, 1210, 1072, 1027, 817, 792, 752, 696, and 525 cm$^{-1}$. $^1$H NMR (DMSO-d$_6$) δ 0.76–0.88 (m), 1.10–1.27 (m, 8H), 2.01 (m, 4H), 2.7–3.5 (m, 8H), 5.24 (s, 1H), 6.8–7.2 (m, 10H), and 7.5–7.9 (m, 4H).

EXAMPLE 13

Singlet Oxygen Production by 7-(1,2-dihydro-1,2-methano[60]fullerene-61-(1,1-dicyanoethylene))-9,9diethyl-2-diphenylaminofluorene upon laser irradiation Direct measurement of singlet oxygen was carried out by the detection of its luminescence emission at 1270 nm corresponding to $^1\Delta_g$ to $^3\Sigma_g$ transitions of molecular oxygen. The measurement was accomplished using a highly sensitive photon multiplier tube (PMT) detector coupled with 4 bandpass filters (1200, 1270, 1300, and 1330 nm) and monitored in the near infrared region. The PMT output was amplified and converted to a voltage pulse using a high-speed current preamplifier. A multichannel scaler connected to a personal computer was used for time-resolved single photon counting, with a typical temporal resolution of 80 ns. A photosensitizer sample solution of 7-(1,2-dihydro-1,2-methano[60]fullerene-61-(1,1-dicyanoethylene))-9,9diethyl-2-diphenylaminofluorene (0.1 mg/ml, DMF) in a quartz cuvette was irradiated by a tunable pulsed laser system with the excitation wavelength of 532 nm and the irradiation spot size of 3 mm in diameter. The pulse energy (630 nm) applied to the sample is roughly 1.0 mJ and the photoemission at 1,270 nm was detected and counted in intensity as the sum of photon emission over 1,000–65,000 laser pulse records. A time-resolved signal measurement, with a laser pulse length of 20 nsec and duration of 0.1 sec between each pulse, was utilized to follow the decay of $^1O_2$ over a time period of 40 μsec. An unexpectedly large amount of singlet oxygen and oxygenated radicals generated from fullerene derivatives or composites were observed.

In vitro studies were conducted by methods described in the literature to assess the direct or indirect oxidative damage of biomolecules, including selective DNA cleavage (see Boutorine et al., *Angew. Chem. Int. Ed. Engl.* 1994, 33, 2462–2464; and Irie et al., *Biosci. Biotech. Biochem.* 1996, 60, 1359–1361.), and membrane lipid peroxidation (see Sera et al., *Carcinogenesis* 1996, 17, 2163–2169). In vivo studies were also conducted to assess the antitumoral activity by methods described in Yasuhiko et al., *Jpn. J. Cancer Res.* 1997, 88, 1108–1116; and Chi et al., *Proc. Electrochem. Soc.* 1999, 99-12, 234–249. The results show that the tested fullrene compound was unexpectedly effective in inhibiting the growth of tumor cells.

OTHER EMBODIMENTS

A number of embodiments of the invention have been described. Nevertheless, it will be understood that various modifications may be made without departing from the spirit and scope of the invention. Accordingly, other embodiments are within the scope of the following claims.

What is claimed is:

1. A compound of the following formula:

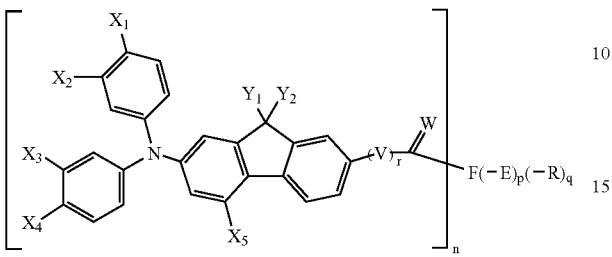

wherein
F is a fullerene core;
E is $Y_1,Y_2$-amino, $Y_2$-amino, $(Y_1,Y_2$-alkyl)-amino, $Y_1,Y_2$-ethylenediamino, (dihydroxymethyl)alkylamino, $(X_1,X_3$-aryl)amino, $X_1,X_3$-aryloxy, $Y_2$-alkoxy, $Y_1,Y_2$-alkoxy, $(Y_1,Y_2$-amino)alkoxy, $(Y_1,Y_2,Y_3$-aryl)oxy, (dihydroxyalkyl)-aryloxy, $(Y_1,Y_2,Y_3$-alkyl)amino, $(Y_1,Y_2,Y_3$-aryl)amino, dihydroxyalkylamino, $Y_1,Y_2,Y_3$-alkoxy, (trihydroxyalkyl)alkoxy, (trihydroxyalkyl)alkylamino, (dicarboxyalkyl)amino, $Y_2$-thio, $(Y_1,Y_2,Y_3$-alkyl)thio, $(X_1,X_3$-aryl)thio, $(Y_1,Y_2$-alkyl)thio, (dihydroxyalkyl)thio, $Y_1$, $Y_2$-dioxoalkyl, tri-$(Y_1,Y_2,Y_3$-methylaminocarboxyethyl)methylamino, ((glycosidyl)oxoheteroaryl)amino, ((glycosidyl)oxoaryl)amino, $(X_1,X_2,X_3$-heteroaryl)amino, $(X_1$-diarylketone)amino, $(T,X_1$-oxoaryl)amino, $(T,X_1$-dioxoaryl)amino, $(Y_1$-alkyl,$Y_2$-alkyldioxoheteroaryl)amino, $(Y_1$-alkyl,$Y_2$-alkyldioxoaryl)amino, (di$(Y_1,Y_2$-methyl)dioxoheteroaryl)amino, (di$(Y_1,Y_2$-methyl)dioxoaryl)amino, ((glycosidyl)heteroaryl)amino, ((glycosidyl)aryl)amino, ((carboxylacetylalkyl)oxoheteroaryl) amino, ((carboxylacetylalkyl)oxoaryl)amino, ((isopropylaminohydroxy-alkoxy) aryl)amino, $(X_1,X_2,X_3$-alkylaryl)amino, $(X_1,X_2,X_3$-heteroaryl)oxy, (isopropylaminohydroxyalkyl)aryloxy, $(X_1,X_2,X_3$-oxoheteroaryl)oxy, $(X_1,X_2,X_3$-oxoaryl)oxy, $(X_1,Y_1$-oxoheteroaryl)oxy, $(X_1$-diarylketone)oxy, $(T,X_1$-oxoaryl)oxy, $(X_1,X_2$-dioxoaryl)oxy, $(Y_1,Y_2$,di-aminodihydroxy)alkyl, $(X_1,X_2$-heteroaryl)thio, ((tricarboxylalkyl)ethylene-diamino)alkoxy, $(X_1,X_2$-oxoaryl)thio, $(X_1,X_2$-dioxoaryl)thio, (glycosidylheteroaryl)thio, (glycosidylaryl)thio, $Y_1$-alkyl(thiocarbonyl)thio, $Y_1,Y_2$-alkyl (thiocarbonyl)thio, $Y_1,Y_2,Y_3$-alkyl(thiocarbonyl)thio, $(Y_1,Y_2$-aminothiocarbonyl) thio, (pyranosyl)thio, cysteinyl, tyrosinyl, (phenylalainyl)amino, (dicarboxyalkyl)thio, (aminoaryl)$_{1-100}$amino, (pyranosyl)$_{1-100}$amino, $(Y_1$-aminoaryl)$_{1-100}$amino, (amino (sulfoaryl))$_{T100}$amino, peptidyl, thymidinyl, uridinyl, guanosinyl, adenosinyl, cholesteryl, or biotinylalkoxy;
each T, independently, being halo;
each of $X_1$, $X_2$, $X_3$, $X_4$, and $X_5$, independently, is $-Y_2$, $-O-Y_2$, $-S-Y_2$, $-NH-Y_2$, $-CO-O-Y_2$, $-O-CO-Y_2$, $-CO-NH-Y_2$, $-CO-NY_1Y_2$, $-NH-CO-Y_2$, $-SO_2-Y_2$, $-SO_2-O-Y_2$, $-CHY_1Y_2-NY_1Y_2$;
each of $Y_1$, $Y_2$, and $Y_3$, independently or taken together, is $-B-Z$ or $-Z$; in which each B, independently, is $-R^a-O-[Si(CH_3)_2-O-]_{1-100}$, $C_{1-2000}$ alkyl, $C_{6-40}$ aryl, $C_{7-2000}$ alkylaryl, $C_{7-2000}$ arylalkyl, $(C_{1-30}$ alkyl ether)$_{1-100}$, $(C_{6-40}$ aryl ether)$_{1-100}$, $(C_{7-2000}$ alkylaryl ether)$_{1-100}$, $(C_{7-2000}$ arylalkyl ether)$_{1-100}$, $(C_{1-30}$ alkyl thioether)$_{1-100}$, $(C_{6-40}$ aryl thioether)$_{1-100}$, $(C_{7-2000}$ alkylaryl thioether)$_{1-100}$, $(C_{7-2000}$ arylalkyl thioether)$_{1-100}$, $(C_{2-50}$ alkyl ester)$_{1-100}$, $(C_{7-2000}$ aryl ester)$_{1-100}$, $(C_{8-2000}$ alkylaryl ester)$_{1-100}$, $(C_{8-2000}$ arylalkyl ester)$_{1-100}$, $-R^a-CO-O-(C_{1-30}$ alkyl ether)$_{1-100}$, $-R^a-CO-O-(C_{6-40}$ aryl ether)$_{1-100}$, $-R^a-CO-O-(C_{7-2000}$ alkylaryl ether)$_{1-100}$, $-R^a-CO-O-(C_{7-2000}$ arylalkyl ether)$_{1-100}$, $(C_{4-50}$ alkyl urethane)$_{1-100}$, $(C_{14-60}$ aryl urethane)$_{1-100}$, $(C_{10-2000}$ alkylaryl urethane)$_{1-100}$, $(C_{10-2000}$ arylalkyl urethane)$_{1-100}$, $(C_{5-50}$ alkyl urea)$_{1-100}$, $(C_{14-60}$ aryl urea) $_{1-100}$, $(C_{10-2000}$ alkylaryl urea)$_{1-100}$, $(C_{10-2000}$ arylalkyl urea)$_{1-100}$, $(C_{2-50}$ alkyl amide)$_{1-100}$, $(C_{7-60}$ aryl amide)$_{1-100}$, $(C_{8-2000}$ alkylaryl amide)$_{1-100}$, $(C_{8-2000}$ arylalkyl amide)$_{1-100}$, $(C_{3-30}$ alkyl anhydride)$_{1-100}$, $(C_{8-50}$ aryl anhydride)$_{1-100}$, $(C_{9-2000}$ alkylaryl anhydride)$_{1-100}$, $(C_{9-2000}$ arylalkyl anhydride)$_{1-100}$, $(C_{2-30}$ alkyl carbonate)$_{1-100}$, $(C_{7-50}$ aryl carbonate)$_{1-100}$, $(C_{8-2000}$ alkylaryl carbonate)$_{1-100}$, $(C_{8-2000}$ arylalkyl carbonate)$_{1-100}$, $-R^a-O-CO-NH-(R^b$ or Ar$-R^b-$Ar)$-NH-CO-O-(C_{1-30}$ alkyl ether, $C_{6-40}$ aryl ether, $C_{7-2000}$ alkylaryl ether, or $C_{7-2000}$ arylalkyl ether)$_{1-100}$, $-R^a-O-CO-NH-(R^b$ or Ar$-R^b-$Ar)$-NH-CO-O-(C_{2-50}$ alkyl ester, $C_{7-60}$ aryl ester, $C_{8-2000}$ alkylaryl ester, or $C_{8-2000}$ arylalkyl ester)$_{1-100}$, $-R^a-O-CO-NH-(R^b$ or Ar$-R^b-$Ar)$-NH-CO-O-(_{1-30}$ alkyl ether, $C_{6-40}$ aryl ether, $C_{7-2000}$ alkylaryl ether, or $C_{7-2000}$ arylalkyl ether)$^{1-100}$$-CO-NH-(R^b$ or Ar$-R^b-$Ar)$-NH-CO-O-$, $-R^a-O-CO-NH-(R^b$ or Ar$-R^b-$Ar)$-NH-CO-O-(C_{2-50}$ alkyl ester, $C_{7-60}$ aryl ester, $C_{8-2000}$ alkylaryl ester, or $C_{8-2000}$ arylalkyl ester)$^{1-100}$$-R^c-O-CO-NH-(R^b$ or Ar$-R^b-$Ar)$-NH-CO-O-$, $-R^a-NH-CO-NH-(R^b$ or Ar$-R^b-$Ar)$-NH-CO-(C_{1-30}$ alkyl ether, $C_{6-40}$ aryl ether, $C_{7-2000}$ alkylaryl ether, or $C_{7-2000}$ arylalkyl ether)$_{1-100}$, $-R^a-NH-CO-NH-(R^b$ or Ar$-R^b-$Ar)$-NH-CO-O-(C_{2-50}$ alkyl ester, $C_{7-60}$ aryl ester, $C_{8-2000}$ alkylaryl ester, or $C_{8-2000}$ arylalkyl ester)$_{1-100}$, $-R^a-NH-CO-NH-(R^b$ or Ar$-R^b-$Ar)$-NH-CO-O-(C_{1-30}$ alkyl ether, $C_{6-40}$ aryl ether, $C_{7-2000}$ alkylaryl ether, or $C_{7-2000}$ arylalkyl ether)$_{1-100}$$-CO-NH-(R^b$ or Ar$-R^b-$Ar)$-NH-CO-O-$, $-R^a-NH-CO-NH-(R^b$ or Ar$-R^b-$Ar)$-NH-CO-O-(C_{2-50}$ alkyl ester, $C_{7-60}$ aryl ester, $C_{8-2000}$ alkylaryl ester, or $C_{8-2000}$ arylalkyl ester)$^{1-100}$$-R^c-O-CO-NH-(R^b$ or Ar$-R^b-$Ar)$-NH-CO-O-$, $-R^a-O-CO-NH-(R^b$ or Ar$-R^b-$Ar)$-NH-CO-NH-(C_{2-50}$ alkyl amide, $C_{7-60}$ aryl amide, $C_{8-2000}$ alkylaryl amide, or $C_{8-2000}$ arylalkyl amide)$_{1-100}$, or $-R^a-NH-CO-NH-(R^b$ or Ar$-R^b-$Ar)$-NH-CO-NH-(C_{2-50}$ alkyl amide, $C_{7-60}$ aryl amide, $C_{8-2000}$ alkylaryl amide, or $C_{8-2000}$ arylalkyl amide)$_{1-100}$; and
each Z, independently, is $-H$ or $-G-D$, wherein G is $-R^a-$, $-R^a-Ar-$, $-Ar-R^a$, or $-Ar-$; and D is $-H$, $-OH$, $-SH$, $-NH_2$, $-NHOH$, $-SO_3H$, $-OSO_3H$, $-CO_2H$, $-CONH_2$, $-CONHNH_2$, $-CH(NH_2)-CO_2H$, $-NH-CH_2-CO_2H$, $-P(OH)_3$, $-PO(OH)_2$, $-O-PO (OH)_2$, $-O-O-PO (OH)-O-PO(OH)_2$, $-O-PO(O^-)-O-CH_2CH_2NH_3^+$, $-O-PO(O^-)-O-CH_2CH_2-N^{30}(CH_3)_3$, -glycoside, -oligosaccharide, $-CO$-glycoside, $-CO$-oligosaccharide, $-OCH_3$, $-OCH_2(CHOH)_4-CH_2OH$, $-OCH_2(CHOH)_2-CH_2OH$, $-CO-OCH_2$ (CHOH)$_4$—CH$_2$OH, —C$_6$H$_3$(OH)$_2$, —N(CH$_2$CO$_2$H)$_2$, —CO—N(CH$_2$CO$_2$H)$_2$, —CO—NH—C(CH$_2$CH$_2$CO$_2$H)$_3$, —CO—NH—C(CH$_2$CH$_2$OH)$_3$, —[CH$_2$—CH(CO$_2$R$^a$)]$_{1-100}$—H, —NH$_3^+$, —N$^+$H$_2$R$^a$, —N$^+$HR$^a$R$^b$, or —N$^{30}$R$^a$R$^b$R$^c$, each of R$^a$, R$^b$, and R$^c$, independently, being C$_{1-20}$ linear or branched alkyl, and Ar being aryl;

R is hydroxy or amino;

W is O, C(CN)$_2$, N$^+$Y$_1$Y$_2$, or V;

V is C$_{5-20}$ aryl or C$_{2-20}$ heteroaryl;

n is 1–10;

p is 0–20;

q is 0–20; and r is 0.

2. The compound of claim 1, wherein F is a fullerene core of C$_{60}$, C$_{70}$, C$_{76}$, C$_{78}$, C$_{82}$, C$_{84}$, C$_{92}$ (methano)$_n$C$_{60}$, (pyrrolidino)$_n$C$_{60}$, La@C$_s$, Ho@C$_s$, Gd@C$_s$, or Er@C$_s$, in which n is 1–10, and s is 60, 74, or 82.

3. The compound of claim 2, wherein F is a fullerene core of C$_{60}$, C$_{70}$, or C$_{84}$.

4. The compound of claim 1, wherein each of X$_1$, X$_2$, X$_3$, X$_4$, and X$_5$, independently, is hydrogen.

5. The compound of claim 1, wherein each of Y$_1$, Y$_2$, and Y$_3$, independently, is hydrogen, C$_{1-2000}$ alkyl, C$_{6-40}$ aryl, or C$_{7-2000}$ arylalkyl, optioanlly substituted with —OH, —SH, —NH$_2$, —NHOH, —SO$_3$H, —OSO$_3$H, —CO$_2$H, —CONH$_2$, —CONHNH$_2$, —CH(NH$_2$)—CO$_2$H, —NH—CH$_2$—CO$_2$H, —NH$_3^+$, —N$^+$H$_2$R$^a$, —N$^+$HR$^a$R$^b$, or —N$^+$R$^a$R$^b$R$^c$.

6. The compound of claim 1, wherein each of Y$_1$, Y$_2$, and Y$_3$, independently, is ethyl, hydroxyethyl, methoxyethyl, solfonylbutoxyethyl, hydroxycarbonylmethyl, or hydroxycarbonylethyl.

7. The compound of claim 1, wherein W is O, C(CN)$_2$, heteroaryl, N$^+$Y$_1$Y$_2$, each of Y$_1$ and Y$_2$, independently, being hydrogen, alkyl, aryl, or heteroaryl, or, together, being ary or heteroaryl.

8. The compound of claim 7, wherein W is O, C(CN)$_2$,

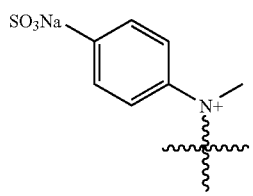
,
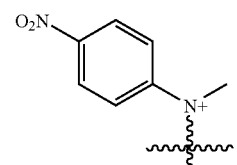
,

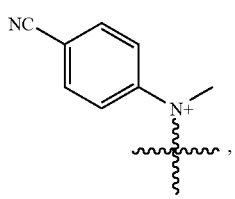
,
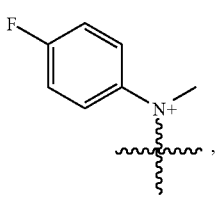
,

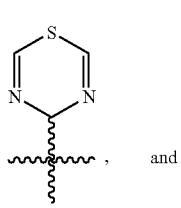
, and
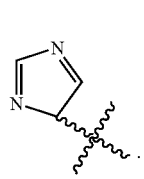
.

9. The compound of claim 1, wherein E is Y$_1$,Y$_2$-amino, Y$_2$-amino, (Y$_1$,Y$_2$-alkyl)-amino, Y$_1$,Y$_2$-ethylenediamino, (dihydroxymethyl)alkylamino, (X$_1$,X$_3$-aryl)amino, (Y$_1$,Y$_2$,Y$_3$-alkyl)amino, (Y$_1$,Y$_2$,Y$_3$-aryl)amino, dihydroxyalkylamino, (trihydroxyalkyl)alkylamino, or (dicarboxyalkyl)amino; and p is 1–4.

10. The compound of claim 9, wherein E is diphenylamino.

11. The compound of claim 1, wherein R is hydroxy or amino.

12. The compound of claim 1, wherein q is 0.

13. The compound of claim 1, wherein the compound is of the following structure of F(—M)$_n$, in which F is a fullerene core of C$_{60}$, n is 1–6, each M, independently, is

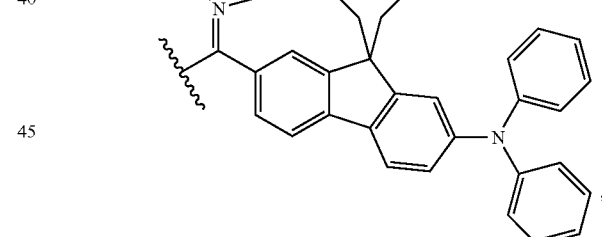
,

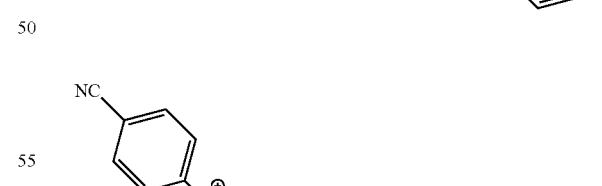
,

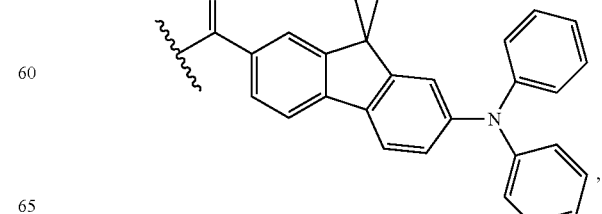
,

-continued
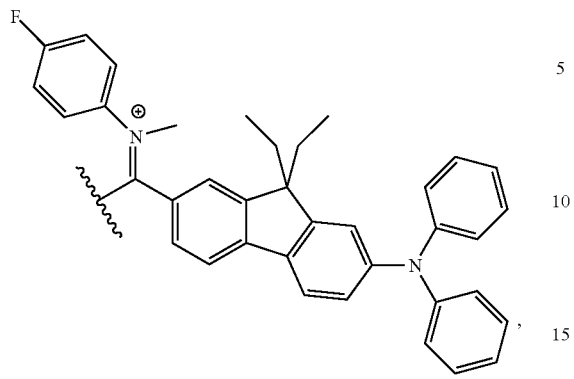
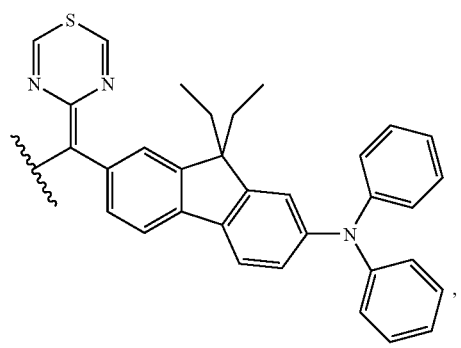
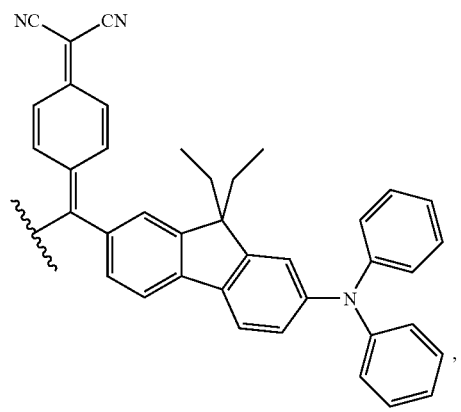
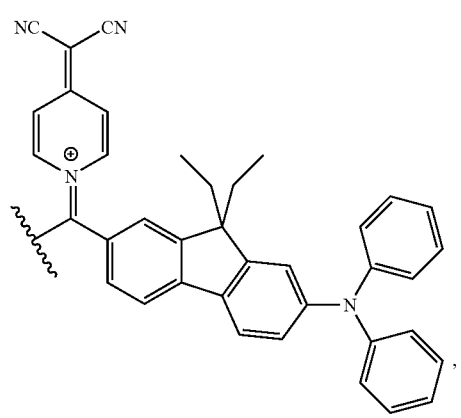
-continued
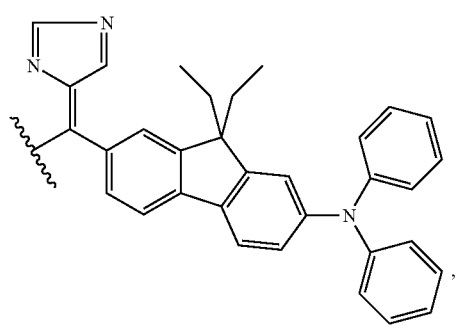
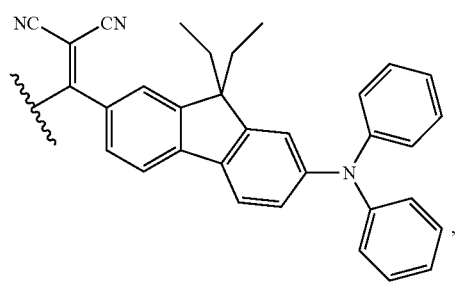
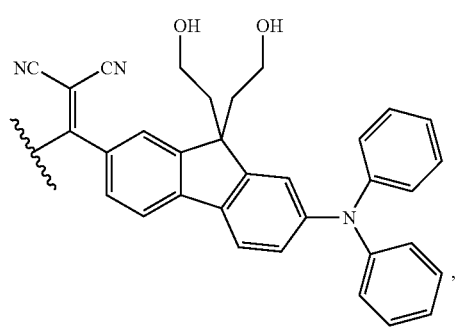
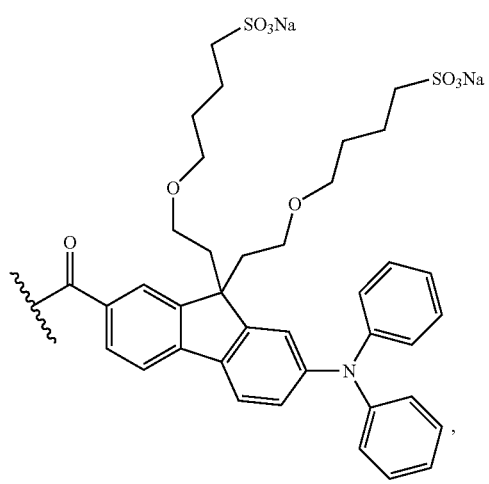

-continued
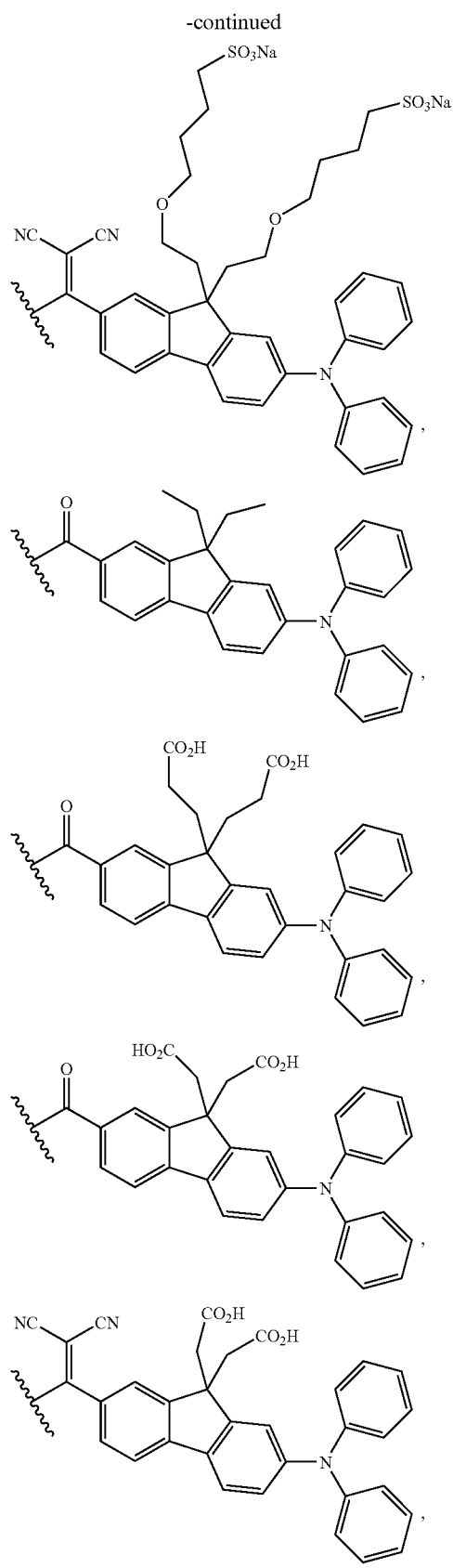
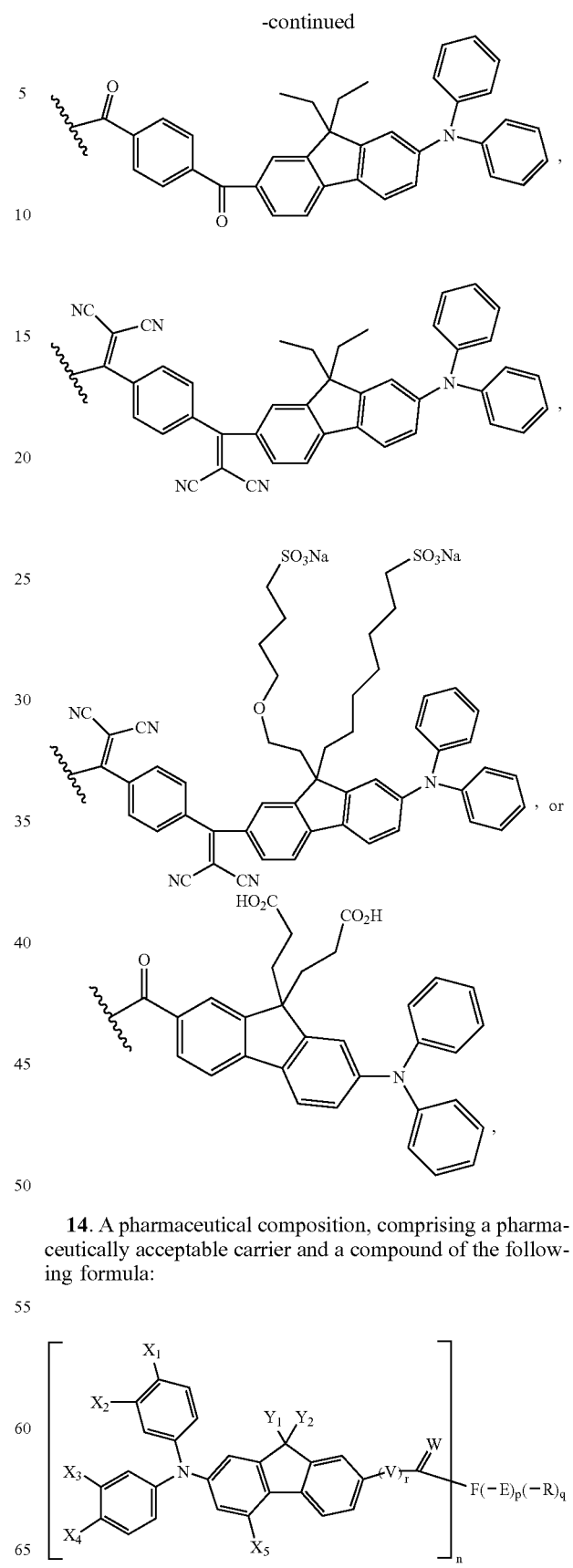
14. A pharmaceutical composition, comprising a pharmaceutically acceptable carrier and a compound of the following formula:

wherein

F is a fullerene core;

E is $Y_1,Y_2$-amino, $Y_2$-amino, $(Y_1,Y_2$-alkyl)-amino, $Y_1,Y_2$-ethylenediamino, (dihydroxymethyl)alkylamino, $(X_1,X_3$-aryl)amino, $X_1,X_3$-aryloxy, $Y_2$-alkoxy, $Y_1,Y_2$-alkoxy, $(Y_1,Y_2$-amino)alkoxy, $(Y_1,Y_2,Y_3$-aryl)oxy, (dihydroxyalkyl)-aryloxy, $(Y_1,Y_2,Y_3$-alkyl)amino, $(Y_1,Y_2,Y_3$-aryl)amino, dihydroxyalkylamino, $Y_1,Y_2,Y_3$-alkoxy, (trihydroxyalkyl)alkoxy, (trihydroxyalkyl)alkylamino, (dicarboxyalkyl)amino, $Y_2$-thio, $(Y_1,Y_2,Y_3$-alkyl)thio, $(X_1,X_3$-aryl)thio, $(Y_1,Y_2$-alkyl)thio, (dihydroxyalkyl)thio, $Y_1,Y_2$-dioxoalkyl, tri-$(Y_1,Y_2,Y_3$-methylaminocarboxyethyl)methylamino, ((glycosidyl)oxoheteroaryl)amino, ((glycosidyl)oxoaryl)amino, $(X_1,X_2,X_3$-heteroaryl)amino, $(X_1$-diarylketone)amino, $(T,X_1$-oxoaryl)amino, $(T,X_1$-dioxoaryl)amino, $(Y_1$-alkyl,$Y_2$-alkyldioxoheteroaryl)amino, $(Y_1$-alkyl,$Y_2$-alkyldioxoaryl)amino, (di($Y_1,Y_2$-methyl)dioxoheteroaryl)amino, (di($Y_1,Y_2$-methyl)dioxoaryl)amino, ((glycosidyl)heteroaryl)amino, ((glycosidyl)aryl)amino, ((carboxylacetylalkyl)oxoheteroaryl)amino, ((carboxylacetylalkyl)oxoaryl)amino, ((isopropylaminohydroxy-alkoxy)aryl)amino, $(X_1,X_2,X_3$-alkylaryl)amino, $(X_1,X_2,X_3$-heteroaryl)oxy, (isopropylaminohydroxyalkyl)aryloxy, $(X_1,X_2,X_3$-oxoheteroaryl)oxy, $(X_1,X_2,X_3$-oxoaryl)oxy, $(X_1,Y_1$-oxoheteroaryl)oxy, $(X_1$-diarylketone)oxy, $(T,X_1$-oxoaryl)oxy, $(X_1,X_2$-dioxoaryl)oxy, $(Y_1,Y_2,$diaminodihydroxy)alkyl, $(X_1,X_2$-heteroaryl)thio, ((tricarboxylalkyl)ethylene-diamino)alkoxy, $(X_1,X_2$-oxoaryl)thio, $(X_1,X_2$-dioxoaryl)thio, (glycosidylheteroaryl)thio, (glycosidylaryl)thio, $Y_1$-alkyl(thiocarbonyl)thio, $Y_1,Y_2$,-alkyl(thiocarbonyl)thio, $Y_1,Y_2,Y_3$-alkyl(thiocarbonyl)thio, $(Y_1,Y_2$-aminothiocarbonyl)thio (pyranosyl)thio, cysteinyl, tyrosinyl, (phenylalainyl)amino, (dicarboxyalkyl)thio, (aminoaryl)$_{1-100}$amino, (pyranosyl)$_{1-100}$amino, $(Y_1$-aminoaryl)$_{1-100}$amino, (amino(sulfoaryl))$_{T100}$amino, peptidyl, thymidinyl, uridinyl, guanosinyl, adenosinyl, cholesteryl, or biotinylalkoxy; each T, independently, being halo;

each of $X_1$, $X_2$, $X_3$, $X_4$, and $X_5$, independently, is $-Y_2$, $-O-Y_2$, $-S-Y_2$, $-NH-Y_2$, $-CO-O-Y_2$, $-O-CO-Y_2$, $-CO-NH-Y_2$, $-CO-NY_1Y_2$, $-NH-CO-Y_2$, $-SO_2-Y_2$, $-SO_2-O-Y_2$, $-CHY_1Y_2-NY_1Y_2$;

each of $Y_1$, $Y_2$, and $Y_3$, independently or taken together, is $-B-Z$ or $-Z$; in which each B, independently, is $-R^a-O-[Si(CH_3)_2-O-]_{1-100}$, $C_{1-2000}$ alkyl, $C_{6-40}$ aryl, $C_{7-2000}$ alkylaryl, $C_{7-2000}$ arylalkyl, $(C_{1-30}$ alkyl ether)$_{1-100}$, $(C_{6-40}$ aryl ether)$_{1-100}$, $(C_{7-2000}$ alkylaryl ether)$_{1-100}$, $(C_{7-2000}$ arylalkyl ether)$_{1-100}$, $(C_{1-30}$ alkyl thioether)$_{1-100}$, $(C_{6-40}$ aryl thioether)$_{1-100}$, $(C_{7-2000}$ alkylaryl thioether)$_{1-100}$, $(C_{7-2000}$ arylalkyl thioether)$_{1-100}$, $(C_{2-50}$ alkyl ester)$_{1-100}$, $(C_{7-2000}$ aryl ester)$_{1-100}$, $(C_{8-2000}$ alkylaryl ester)$_{1-100}$, $(C_{8-2000}$ arylalkyl ester)$_{1-100}$, $-R^a-CO-O-(C_{1-30}$ alkyl ether)$_{1-100}$, $-R^a-CO-O-(C_{6-40}$ aryl ether)$_{1-100}$, $-R^a-CO-O-(C_{7-2000}$ alkylaryl ether)$_{1-100}$, $-R^a-CO-O-(C_{7-2000}$ arylalkyl ether)$_{1-100}$, $(C_{4-50}$ alkyl urethane)$_{1-100}$, $(C_{14-60}$ aryl urethane)$_{1-100}$, $(C_{10-2000}$ alkylaryl urethane)$_{1-100}$, $(C_{10-2000}$ arylalkyl urethane)$_{1-100}$, $(C_{5-50}$ alkyl urea)$_{1-100}$, $(C_{14-60}$ aryl urea)$_{1-100}$, $(C_{10-2000}$ alkylaryl urea)$_{1-100}$, $(C_{10-2000}$ arylalkyl urea)$_{1-100}$, $(C_{2-50}$ alkyl amide)$_{1-100}$, $(C_{7-60}$ aryl amide)$_{1-100}$, $(C_{8-2000}$ alkylaryl amide)$_{1-100}$, $(C_{8-2000}$ arylalkyl amide)$_{1-100}$, $(C_{3-30}$ alkyl anhydride)$_{1-100}$, $(C_{8-50}$ aryl anhydride)$_{1-100}$, $(C_{9-2000}$ alkylaryl anhydride)$_{1-100}$, $(C_{9-2000}$ arylalkyl anhydride)$_{1-100}$, $(C_{2-30}$ alkyl carbonate)$_{1-100}$, $(C_{7-50}$ aryl carbonate)$_{1-100}$, $(C_{8-2000}$ alkylaryl carbonate)$_{1-100}$, $(C_{8-2000}$ arylalkyl carbonate)$_{1-100}$, $-R^a-O-CO-NH-(R^b$ or $Ar-R^b-Ar)-NH-CO-O-(C_{1-30}$ alkyl ether, $C_{6-40}$ aryl ether, $C_{7-2000}$ alkylaryl ether, or $C_{7-2000}$ arylalkyl ether)$_{1-100}$, $-R^a-O-CO-NH-(R^b$ or $Ar-R^b-Ar)-NH-CO-O-(C_{2-50}$ alkyl ester, $C_{7-60}$ aryl ester, $C_{8-2000}$ alkylaryl ester, or $C_{8-2000}$ arylalkyl ester)$_{1-100}$, $-R^a-O-CO-NH-(R^b$ or $Ar-R^b-Ar)-NH-CO-O-(_{1-30}$ alkyl ether, $C_{6-40}$ aryl ether, $C_{7-2000}$ alkylaryl ether, or $C_{7-2000}$ arylalkyl ether)$^{1-100}-CO-NH-(R^b$ or $Ar-R^b-Ar)-NH-CO-O-$, $-R^a-O-CO-NH-(R^b$ or $Ar-R^b-Ar)-NH-CO-O-(C_{2-50}$ alkyl ester, $C_{7-60}$ aryl ester, $C_{8-2000}$ alkylaryl ester, or $C_{8-2000}$ arylalkyl ester)$^{1-100}-R^c-O-CO-NH-(R^b$ or $Ar-R^b-Ar)-NH-CO-O-$, $-R^a-NH-CO-NH-(R^b$ or $Ar-R^b-Ar)-NH-CO-(C_{1-30}$ alkyl ether, $C_{6-40}$ aryl ether, $C_{7-2000}$ alkylaryl ether, or $C_{7-2000}$ arylalkyl ether)$_{1-100}$, $-R^a-NH-CO-NH-(R^b$ or $Ar-R^b-Ar)-NH-CO-O-(C_{2-50}$ alkyl ester, $C_{7-60}$ aryl ester, $C_{8-2000}$ alkylaryl ester, or $C_{8-2000}$ arylalkyl ester)$_{1-100}$, $-R^a-NH-CO-NH-(R^b$ or $Ar-R^b-Ar)-NH-CO-O-(C_{1-30}$ alkyl ether, $C_{6-40}$ aryl ether, $C_{7-2000}$ alkylaryl ether, or $C_{7-2000}$ arylalkyl ether)$_{1-100}-CO-NH-(R^b$ or $Ar-R^b-Ar)-NH-CO-O-$, $-R^a-NH-CO-NH-(R^b$ or $Ar-R^b-Ar)-NH-CO-O-(C_{2-50}$ alkyl ester, $C_{7-60}$ aryl ester, $C_{8-2000}$ alkylaryl ester, or $C_{8-2000}$ arylalkyl ester)$^{1-100}-R^c-O-CO-NH-(R^b$ or $Ar-R^b-Ar)-NH-CO-O-$, $-R^a-O-CO-NH-(R^b$ or $Ar-R^b-Ar)-NH-CO-NH-(C_{2-50}$ alkyl amide, $C_{7-60}$ aryl amide, $C_{8-2000}$ alkylaryl amide, or $C_{8-2000}$ arylalkyl amide)$_{1-100}$, or $-R^a-NH-CO-NH-(R^b$ or $Ar-R^b-Ar)-NH-CO-NH-(C_{2-50}$ alkyl amide, $C_{7-60}$ aryl amide, $C_{8-2000}$ alkylaryl amide, or $C_{8-2000}$ arylalkyl amide)$_{1-100}$; and each Z, independently, is $-H$ or $-G-D$, wherein G is $-R^a-$, $-R^a-Ar-$, $-Ar-R^a$, or $-Ar-$; and D is $-H$, $-OH$, $-SH$, $-NH_2$, $-NHOH$, $-SO_3H$, $-OSO_3H$, $-CO_2H$, $-CONH_2$, $-CONHNH_2$, $-CH(NH_2)-CO_2H$, $-NH-CH_2-CO_2H$, $-P(OH)_3$, $-PO(OH)_2$, $-O-PO(OH)_2$, $-O-PO(OH)-O-PO(OH)_2$, $-O-PO(O^-)-O-CH_2CH_2NH_3^+$, $-O-PO(O^-)-O-CH_2CH_2-N^{30}(CH_3)_3$, -glycoside, -oligosaccharide, $-CO$-glycoside, $-CO$-oligosaccharide, $-OCH_3$, $-OCH_2(CHOH)_4-CH_2OH$, $-OCH_2(CHOH)_2-CH_2OH$, $-CO-OCH_2(CHOH)_4-CH_2OH$, $-C_6H_3(OH)_2$, $-N(CH_2CO_2H)_2$, $-CO-N(CH_2CO_2H)_2$, $-CO-NH-C(CH_2CH_2CO_2H)_3$, $-CO-NH-C(CH_2OH)_3$, $-[CH_2-CH(CO_2R^a)]_{1-100}-H$, $-NH_3^+$, $-N^+H_2R^a$, $-N^+HR^aR^b$, or $-N^{30}R^aR^bR^c$, each of $R^a$, $R^b$, and $R^c$, independently, being $C_{1-20}$ linear or branched alkyl, and Ar being aryl;

R is alkyl, hydroxy, or amino;

W is O, $C(CN)_2$, $N^+Y_1Y_2$, or V;

V is $C_{5-20}$ aryl or $C_{2-20}$ heteroaryl;

n is 1–10;

p is 0–20;

q is 0–20; and r is 0.

15. The pharmaceutical composition of claim 14, wherein F is a fullerene core of $C_{60}$, $C_{70}$, $C_{76}$, $C_{78}$, $C_{82}$, $C_{84}$, $C_{92}$ (methano)$_n$C$_{60}$, (pyrrolidino)$_n$C$_{60}$, La@C$_s$, Ho@C$_s$, Gd@C$_s$, or Er@C3, in which n is 1–10, and s is 60, 74, or 82.

16. The pharmaceutical composition of claim 14, wherein each of X$_1$, X$_2$, X$_3$, X$_4$, and X$_5$, independently, is hydrogen.

17. The pharmaceutical composition of claim 14, wherein the compound is of the following structure of F(—M), in which F is a fullerene core of C$_{60}$, n is 1–6, each M, independently, is:

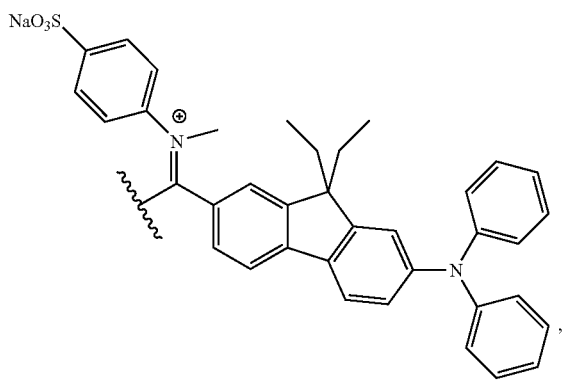

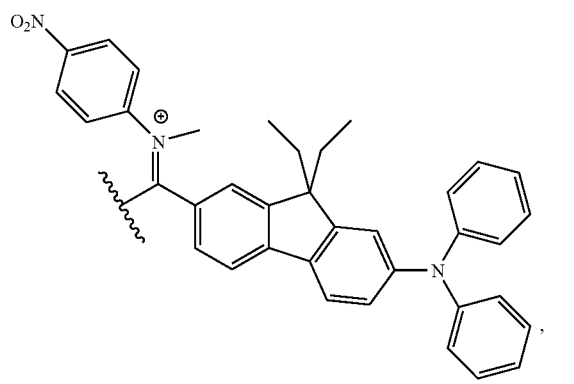

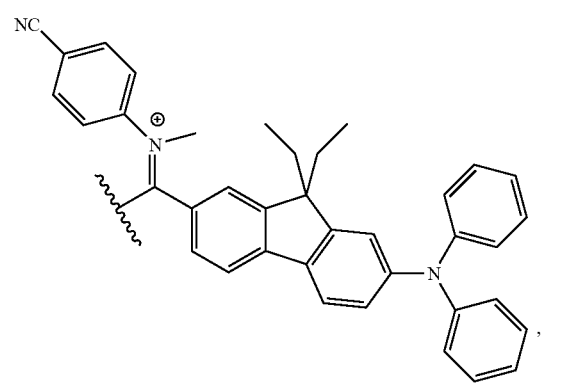

-continued

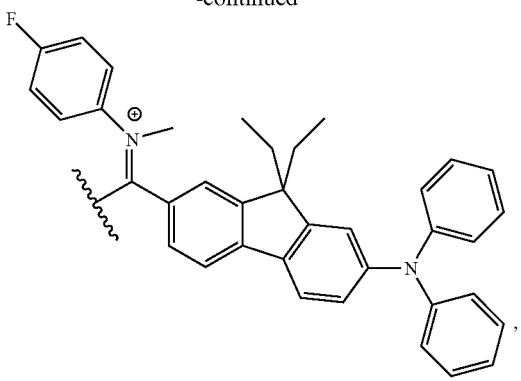

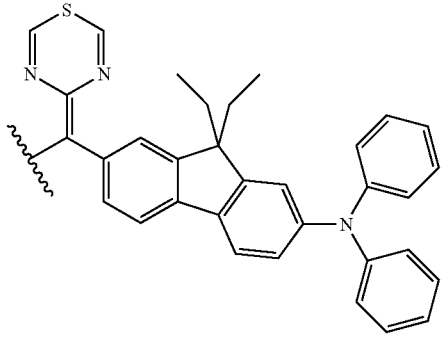

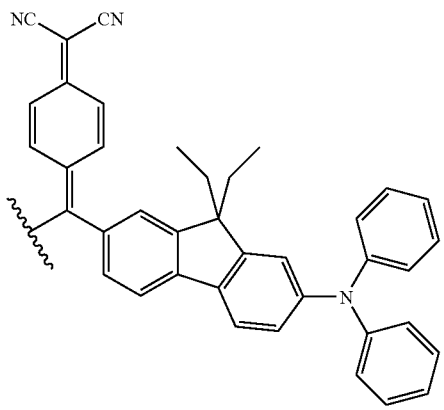

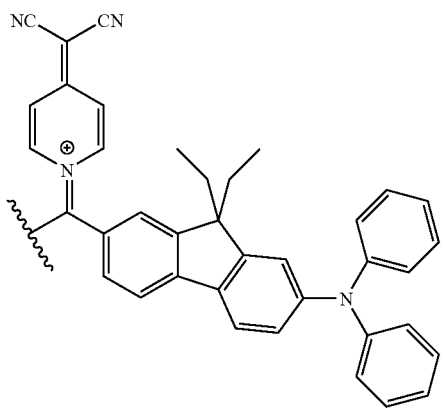

31
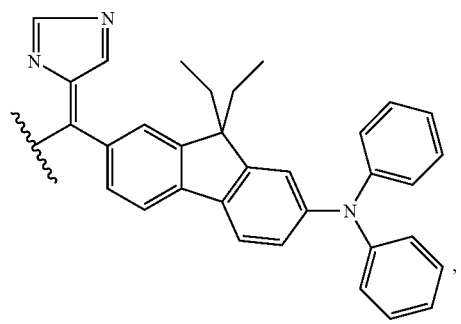
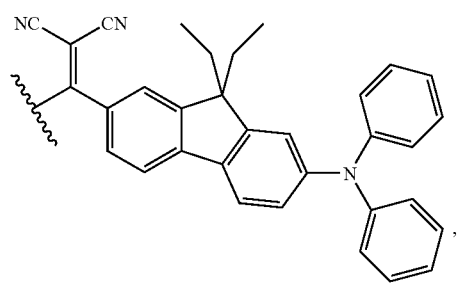
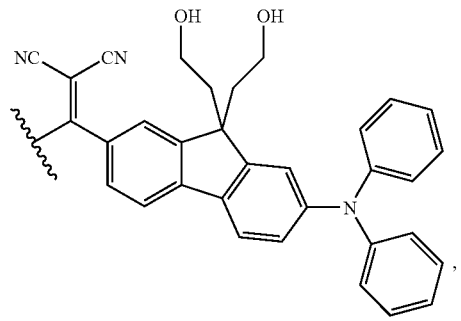
32
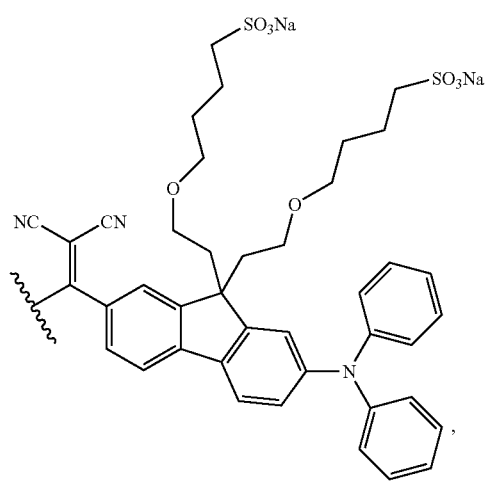
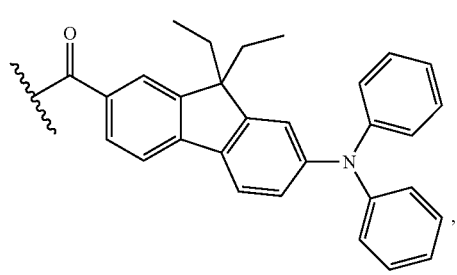
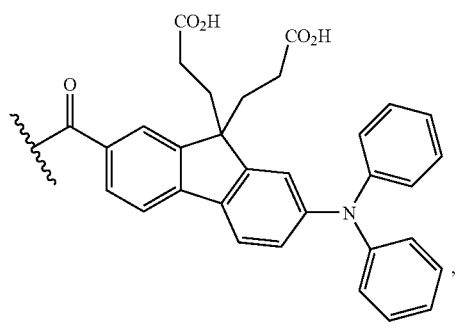
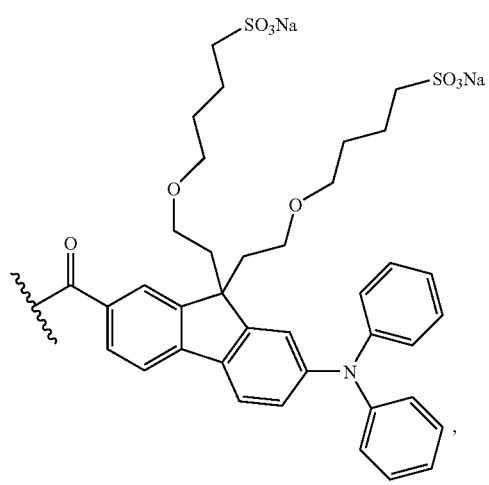

-continued
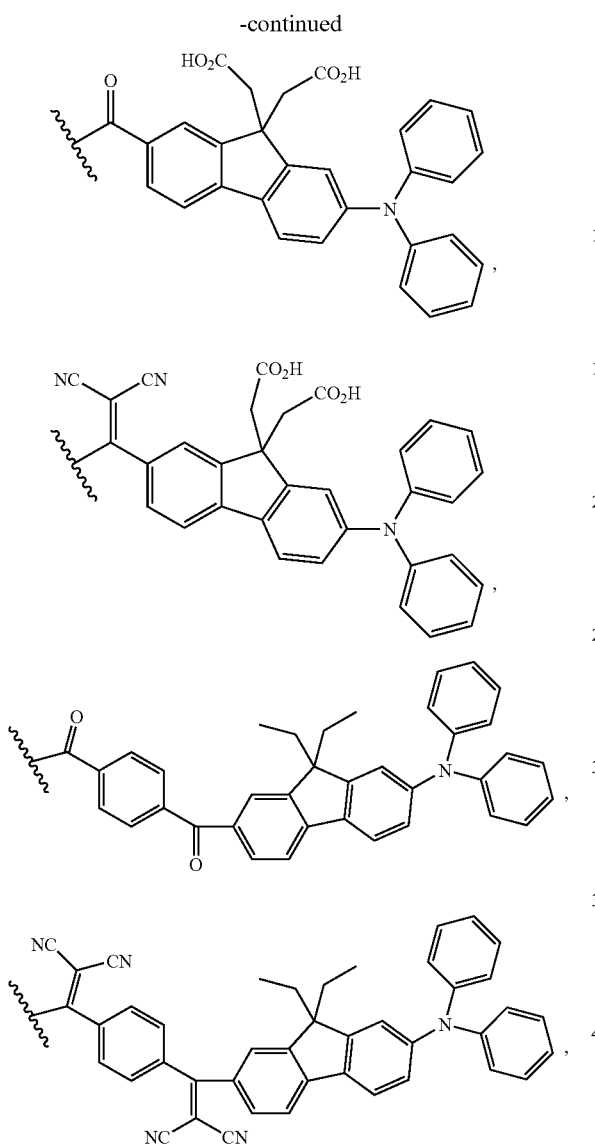
-continued
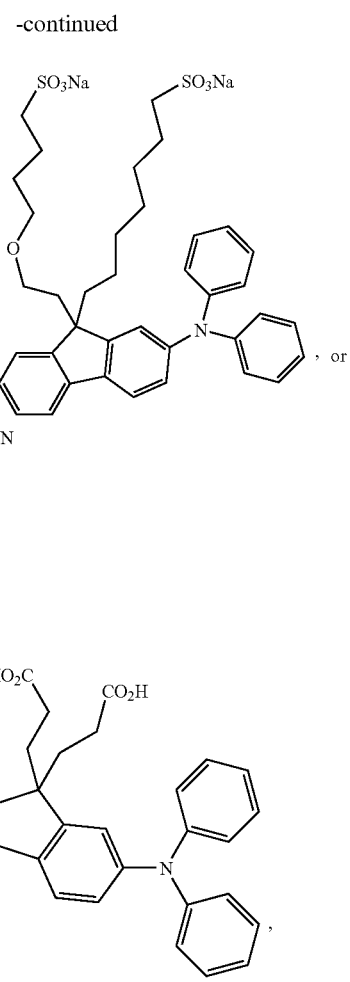
* * * * *